(12) United States Patent
Cruise et al.

(10) Patent No.: US 9,877,731 B2
(45) Date of Patent: *Jan. 30, 2018

(54) EMBOLIZATION DEVICE CONSTRUCTED FROM EXPANSILE POLYMER

(71) Applicant: MicroVention, Inc., Tustin, CA (US)

(72) Inventors: Gregory M. Cruise, Rancho Santa Margarita, CA (US); Michael Constant, Mission Viejo, CA (US); Terrance Tran, Westminster, CA (US); Joseph Gulachenski, Trabuco Canyon, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,135

(22) Filed: Aug. 12, 2016

(65) Prior Publication Data

US 2016/0345978 A1 Dec. 1, 2016

Related U.S. Application Data

(63) Continuation of application No. 13/553,275, filed on Jul. 19, 2012, now Pat. No. 9,451,963, which is a continuation of application No. 11/764,111, filed on Jun. 15, 2007, now Pat. No. 8,377,091.

(60) Provisional application No. 60/814,309, filed on Jun. 15, 2006.

(51) Int. Cl.
| | |
|---|---|
| A61M 29/00 | (2006.01) |
| A61B 17/12 | (2006.01) |
| A61L 31/04 | (2006.01) |
| A61L 31/14 | (2006.01) |
| A61L 31/06 | (2006.01) |
| A61L 31/00 | (2006.01) |

(52) U.S. Cl.
CPC ...... *A61B 17/1219* (2013.01); *A61B 17/1214* (2013.01); *A61B 17/12113* (2013.01); *A61B 17/12145* (2013.01); *A61B 17/12154* (2013.01); *A61B 17/12168* (2013.01); *A61L 31/00* (2013.01); *A61L 31/041* (2013.01); *A61L 31/048* (2013.01); *A61L 31/06* (2013.01); *A61L 31/14* (2013.01); *A61L 31/145* (2013.01); *A61L 31/146* (2013.01); *A61L 2400/04* (2013.01)

(58) Field of Classification Search
None
See application file for complete search history.

(56) References Cited

U.S. PATENT DOCUMENTS

| | | |
|---|---|---|
| 3,709,842 A | 1/1973 | Stoy et al. |
| 3,749,085 A | 7/1973 | Wilson et al. |
| 4,020,829 A | 5/1977 | Wilson et al. |
| 4,301,803 A | 11/1981 | Handa et al. |
| 4,304,232 A | 12/1981 | Michaels |
| 4,365,621 A | 12/1982 | Brundin |
| 4,402,319 A | 9/1983 | Handa et al. |
| 4,493,329 A | 1/1985 | Crawford et al. |
| 4,509,504 A | 4/1985 | Brundin |
| 4,529,739 A | 7/1985 | Scott et al. |
| 4,551,132 A | 11/1985 | Pasztor et al. |
| 4,663,358 A | 5/1987 | Rhyon et al. |
| 4,795,741 A | 1/1989 | Leshchiner et al. |
| 4,819,637 A | 4/1989 | Dormandy, Jr. et al. |
| 4,932,419 A | 6/1990 | de Toledo |
| 4,951,677 A | 8/1990 | Crowley et al. |
| 4,994,069 A | 2/1991 | Ritchart et al. |
| 5,120,349 A | 6/1992 | Stewart et al. |
| 5,122,136 A | 6/1992 | Guglielmi et al. |
| 5,129,180 A | 7/1992 | Stewart |
| 5,133,731 A | 7/1992 | Butler et al. |
| 5,147,646 A | 9/1992 | Graham |
| 5,154,705 A | 10/1992 | Fleischhacker et al. |
| 5,163,952 A | 11/1992 | Froix |
| 5,165,421 A | 11/1992 | Fleischhacker et al. |
| 5,217,484 A | 6/1993 | Marks |
| 5,226,911 A | 7/1993 | Chee et al. |
| 5,258,042 A | 11/1993 | Mehta |
| 5,304,194 A | 4/1994 | Chee et al. |
| 5,312,415 A | 5/1994 | Palermo |
| 5,350,397 A | 9/1994 | Palermo et al. |
| 5,354,290 A | 10/1994 | Gross |

(Continued)

FOREIGN PATENT DOCUMENTS

| | | |
|---|---|---|
| CA | 2551373 C | 6/2014 |
| CN | 102107025 B | 5/2014 |

(Continued)

OTHER PUBLICATIONS

Ahuja et al., Platinum coil coatings to increase thrombogenicity: a preliminary study in rabbits, AJNR, 14: 794-789 (1993).

Almany, Biomaterials, 26, 2005, 2467-2477, Biosynthetic hydrogel scaffolds made from fibrinogen and polyethylene glycol for 3D cell cultures.

Carelli V. et al., "Silicone microspheres for pH-controlled gastro-intestinal drug delivery," 1999, International Journal of Pharmaceutics, V179, pp. 73-83.

(Continued)

*Primary Examiner* — Susan Tran
*Assistant Examiner* — William Craigo
(74) *Attorney, Agent, or Firm* — K&L Gates LLP; Louis C. Cullman; Brian J. Novak

(57) ABSTRACT

Devices for the occlusion of body cavities, such as the embolization of vascular aneurysms and the like, and methods for making and using such devices. The devices may be comprised of novel expansile materials, novel infrastructure design, or both. The devices provided are very flexible and enable deployment with reduced or no damage to bodily tissues, conduits, cavities, etceteras.

18 Claims, 8 Drawing Sheets

(56) References Cited

U.S. PATENT DOCUMENTS

| | | |
|---|---|---|
| 5,373,619 A | 12/1994 | Fleischhacker et al. |
| 5,382,259 A | 1/1995 | Phelps et al. |
| 5,382,260 A | 1/1995 | Dormandy, Jr. et al. |
| 5,443,478 A | 8/1995 | Purdy |
| 5,449,369 A | 9/1995 | Imran |
| 5,456,693 A | 10/1995 | Conston et al. |
| 5,469,867 A | 11/1995 | Schmitt |
| 5,476,472 A | 12/1995 | Dormandy, Jr. et al. |
| 5,483,022 A | 1/1996 | Mar |
| 5,522,822 A | 6/1996 | Phelps et al. |
| 5,525,334 A | 6/1996 | Ito et al. |
| 5,536,274 A | 7/1996 | Neuss |
| 5,541,234 A | 7/1996 | Unger et al. |
| 5,549,624 A | 8/1996 | Mirigian |
| 5,573,520 A | 11/1996 | Schwartz et al. |
| 5,573,994 A | 11/1996 | Kabra et al. |
| 5,578,074 A | 11/1996 | Mirigian |
| 5,580,568 A | 12/1996 | Greff et al. |
| 5,582,610 A | 12/1996 | Grossi et al. |
| 5,582,619 A | 12/1996 | Ken |
| 5,607,417 A | 3/1997 | Batich et al. |
| 5,609,629 A | 3/1997 | Fearnot et al. |
| 5,612,050 A | 3/1997 | Rowe et al. |
| 5,624,461 A | 4/1997 | Mariant |
| 5,624,685 A | 4/1997 | Takahashi et al. |
| 5,634,936 A | 6/1997 | Linden et al. |
| 5,645,558 A | 7/1997 | Horton |
| 5,651,979 A | 7/1997 | Ron et al. |
| 5,658,308 A * | 8/1997 | Snyder ............ A61B 17/12022 606/191 |
| 5,667,767 A | 9/1997 | Greff et al. |
| 5,672,634 A | 9/1997 | Tseng et al. |
| 5,678,296 A | 10/1997 | Fleischhacker et al. |
| 5,690,666 A | 11/1997 | Berenstein et al. |
| 5,690,667 A | 11/1997 | Gia |
| 5,690,671 A | 11/1997 | McGurk et al. |
| 5,695,480 A | 12/1997 | Evans et al. |
| 5,702,361 A | 12/1997 | Evans et al. |
| 5,718,711 A | 2/1998 | Berenstein et al. |
| 5,725,568 A | 3/1998 | Hastings |
| 5,749,894 A | 5/1998 | Engelson |
| 5,750,585 A | 5/1998 | Park et al. |
| 5,752,974 A | 5/1998 | Rhee et al. |
| 5,755,658 A | 5/1998 | Wallace et al. |
| 5,766,160 A | 6/1998 | Samson et al. |
| 5,766,219 A | 6/1998 | Horton |
| 5,823,198 A | 10/1998 | Jones et al. |
| 5,830,178 A | 11/1998 | Jones et al. |
| 5,843,743 A | 12/1998 | Hubbell et al. |
| 5,851,508 A | 12/1998 | Greff et al. |
| 5,853,419 A | 12/1998 | Ken et al. |
| 5,883,705 A | 3/1999 | Minne et al. |
| 5,891,155 A | 4/1999 | Irie |
| 5,952,232 A | 9/1999 | Rothman |
| 5,976,162 A | 11/1999 | Doan et al. |
| 5,980,514 A | 11/1999 | Kupiecki et al. |
| 6,004,338 A | 12/1999 | Ken et al. |
| 6,004,573 A | 12/1999 | Rathi et al. |
| 6,013,084 A | 1/2000 | Ken et al. |
| 6,015,424 A | 1/2000 | Rosenbluth et al. |
| 6,017,977 A | 1/2000 | Evans et al. |
| 6,051,607 A | 4/2000 | Greff |
| 6,063,100 A | 5/2000 | Diaz et al. |
| 6,066,149 A | 5/2000 | Samson et al. |
| 6,093,199 A | 7/2000 | Brown et al. |
| 6,096,034 A | 8/2000 | Kupiecki et al. |
| 6,103,865 A | 8/2000 | Bae et al. |
| 6,136,015 A | 10/2000 | Kurz et al. |
| 6,146,373 A | 11/2000 | Cragg et al. |
| 6,159,165 A | 12/2000 | Ferrera et al. |
| 6,168,570 B1 | 1/2001 | Ferrera |
| 6,171,326 B1 | 1/2001 | Ferrera et al. |
| 6,179,857 B1 | 1/2001 | Diaz et al. |
| 6,187,024 B1 | 2/2001 | Boock et al. |
| 6,193,728 B1 | 2/2001 | Ken et al. |
| 6,201,065 B1 | 3/2001 | Pathak et al. |
| 6,231,590 B1 | 5/2001 | Slaikeu et al. |
| 6,238,403 B1 | 5/2001 | Greene, Jr. et al. |
| 6,245,090 B1 | 6/2001 | Gilson et al. |
| 6,270,748 B1 | 8/2001 | Annan et al. |
| 6,280,457 B1 | 8/2001 | Wallace et al. |
| 6,281,263 B1 | 8/2001 | Evans et al. |
| 6,287,318 B1 | 9/2001 | Villar et al. |
| 6,299,604 B1 | 10/2001 | Ragheb et al. |
| 6,299,619 B1 | 10/2001 | Greene, Jr. et al. |
| 6,299,627 B1 | 10/2001 | Eder et al. |
| 6,303,100 B1 | 10/2001 | Ricci et al. |
| 6,312,421 B1 | 11/2001 | Boock |
| 6,333,020 B1 | 12/2001 | Wallace et al. |
| 6,335,384 B1 | 1/2002 | Evans et al. |
| 6,342,202 B1 | 1/2002 | Evans et al. |
| 6,399,886 B1 | 6/2002 | Avellanet |
| 6,423,085 B1 | 7/2002 | Murayama et al. |
| 6,425,893 B1 | 7/2002 | Guglielmi et al. |
| 6,454,738 B1 | 9/2002 | Tran et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,537,569 B2 | 3/2003 | Cruise et al. |
| 6,558,367 B1 | 5/2003 | Cragg et al. |
| 6,565,551 B1 | 5/2003 | Jones et al. |
| 6,569,190 B2 | 5/2003 | Whalen et al. |
| 6,599,448 B1 | 7/2003 | Ehrhard, Jr. et al. |
| 6,602,261 B2 | 8/2003 | Greene, Jr. et al. |
| 6,605,294 B2 * | 8/2003 | Sawhney ......... A61B 17/12022 424/426 |
| 6,623,450 B1 | 9/2003 | Dutta |
| 6,634,361 B1 | 10/2003 | Nikolchev et al. |
| 6,645,167 B1 | 11/2003 | Whalen et al. |
| 6,684,884 B2 | 2/2004 | Nikolchev et al. |
| 6,699,222 B1 | 3/2004 | Jones et al. |
| 6,723,108 B1 | 4/2004 | Jones et al. |
| 6,756,031 B2 | 6/2004 | Evans et al. |
| 6,759,028 B2 | 7/2004 | Wallace et al. |
| 6,849,081 B2 | 2/2005 | Sepetka et al. |
| 6,860,893 B2 | 3/2005 | Wallace et al. |
| 6,878,384 B2 | 4/2005 | Cruise et al. |
| 6,887,974 B2 | 5/2005 | Pathak et al. |
| 6,962,689 B2 | 11/2005 | Whalen et al. |
| 6,964,657 B2 | 11/2005 | Cragg et al. |
| 7,018,365 B2 | 3/2006 | Strauss et al. |
| 7,033,374 B2 | 4/2006 | Schaefer et al. |
| 7,066,904 B2 | 6/2006 | Rosenthal et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,422,569 B2 | 9/2008 | Wilson et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,976,527 B2 | 7/2011 | Cragg et al. |
| 7,988,992 B2 | 8/2011 | Omidian et al. |
| 8,066,667 B2 | 11/2011 | Hayman et al. |
| 8,235,941 B2 | 8/2012 | Hayman et al. |
| 8,377,091 B2 | 2/2013 | Cruise et al. |
| 8,454,649 B2 | 6/2013 | Cragg et al. |
| 8,486,046 B2 | 7/2013 | Hayman et al. |
| 9,011,884 B2 | 4/2015 | Constant et al. |
| 2001/0023325 A1 | 9/2001 | Ferrera |
| 2002/0026234 A1 | 2/2002 | Li et al. |
| 2002/0042378 A1 | 4/2002 | Reich et al. |
| 2002/0169473 A1 | 11/2002 | Sepetka et al. |
| 2002/0176880 A1 | 11/2002 | Cruise et al. |
| 2003/0021762 A1 | 1/2003 | Luthra |
| 2003/0077272 A1 | 4/2003 | Pathak et al. |
| 2003/0078339 A1 | 4/2003 | Kiser et al. |
| 2003/0086874 A1 | 5/2003 | Whalen, II et al. |
| 2003/0100942 A1 | 5/2003 | Ken et al. |
| 2003/0134032 A1 | 7/2003 | Chaouk |
| 2003/0203991 A1 | 10/2003 | Schottman et al. |
| 2003/0211083 A1 | 11/2003 | Vogel et al. |

(56) References Cited

U.S. PATENT DOCUMENTS

| | | |
|---|---|---|
| 2003/0220245 A1 | 11/2003 | Hubbell et al. |
| 2003/0232198 A1 | 12/2003 | Lamberti et al. |
| 2003/0232895 A1 | 12/2003 | Omidian et al. |
| 2004/0006534 A1 | 1/2004 | Schaefer et al. |
| 2004/0024098 A1 | 2/2004 | Mather et al. |
| 2004/0059370 A1 | 3/2004 | Greene et al. |
| 2004/0091543 A1 | 5/2004 | Bell et al. |
| 2004/0098028 A1* | 5/2004 | Martinez .......... A61B 17/12022 606/200 |
| 2004/0115164 A1 | 6/2004 | Pierce et al. |
| 2004/0158282 A1 | 8/2004 | Jones et al. |
| 2004/0209998 A1 | 10/2004 | De Vries |
| 2005/0003010 A1 | 1/2005 | Cohen et al. |
| 2005/0008610 A1 | 1/2005 | Schwarz et al. |
| 2005/0095428 A1 | 5/2005 | DiCarlo et al. |
| 2005/0106119 A1 | 5/2005 | Brandom et al. |
| 2005/0119687 A1 | 6/2005 | Dacey et al. |
| 2005/0143484 A1 | 6/2005 | Fang et al. |
| 2005/0171572 A1 | 8/2005 | Martinez et al. |
| 2005/0175709 A1 | 8/2005 | Baty et al. |
| 2005/0196426 A1 | 9/2005 | Cruise et al. |
| 2005/0196449 A1 | 9/2005 | DiCarlo et al. |
| 2005/0226935 A1 | 10/2005 | Kamath et al. |
| 2005/0281883 A1 | 12/2005 | Daniloff et al. |
| 2006/0052815 A1 | 3/2006 | Fitz et al. |
| 2006/0067883 A1 | 3/2006 | Krom et al. |
| 2006/0074370 A1* | 4/2006 | Zhou ................... A61F 9/00772 604/8 |
| 2006/0233854 A1 | 10/2006 | Seliktar et al. |
| 2007/0026039 A1 | 2/2007 | Drumheller et al. |
| 2007/0196454 A1 | 8/2007 | Stockman et al. |
| 2007/0202046 A1 | 8/2007 | Dave |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237720 A1 | 10/2007 | Padilla et al. |
| 2007/0237741 A1 | 10/2007 | Figuly et al. |
| 2007/0248567 A1 | 10/2007 | Pathak et al. |
| 2007/0254005 A1 | 11/2007 | Pathak et al. |
| 2007/0288084 A1 | 12/2007 | Lee et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0208167 A1 | 8/2008 | Stankus |
| 2008/0226741 A1 | 9/2008 | Richard |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0081275 A1 | 3/2009 | Rolfes et al. |
| 2009/0093550 A1 | 4/2009 | Rolfes et al. |
| 2009/0117033 A1 | 5/2009 | O'Gara |
| 2009/0164013 A1 | 6/2009 | Cruise et al. |
| 2009/0181068 A1 | 7/2009 | Dunn |
| 2009/0221731 A1 | 9/2009 | Vetrecin et al. |
| 2009/0232869 A1 | 9/2009 | Greene |
| 2009/0259302 A1 | 10/2009 | Trollsas et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0086678 A1 | 4/2010 | Arthur et al. |
| 2010/0092533 A1 | 4/2010 | Stopek et al. |
| 2010/0241160 A1 | 9/2010 | Murphy |
| 2010/0247663 A1 | 9/2010 | Day et al. |
| 2010/0249913 A1 | 9/2010 | Datta et al. |
| 2010/0256777 A1 | 10/2010 | Dattta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0091549 A1 | 4/2011 | Blaskovich et al. |
| 2011/0182998 A1 | 7/2011 | Reb et al. |
| 2011/0184455 A1 | 7/2011 | Keeley |
| 2011/0190813 A1 | 8/2011 | Brownlee et al. |
| 2011/0202016 A1 | 8/2011 | Zugates |
| 2011/0212178 A1 | 9/2011 | Constant et al. |
| 2012/0041481 A1 | 2/2012 | Daniloff et al. |
| 2012/0083523 A1 | 4/2012 | Richard et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Bartling et al. |
| 2012/0238644 A1 | 9/2012 | Gong et al. |
| 2012/0244198 A1 | 9/2012 | Malmsjo et al. |
| 2012/0283769 A1 | 11/2012 | Cruise et al. |
| 2012/0289995 A1 | 11/2012 | Constant et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0108574 A1 | 5/2013 | Chevalier et al. |
| 2013/0131716 A1 | 5/2013 | Cruise et al. |
| 2013/0253087 A1 | 9/2013 | Cruise et al. |
| 2014/0056806 A1 | 2/2014 | Vemengo et al. |
| 2014/0274945 A1 | 9/2014 | Blaskovich et al. |
| 2014/0277057 A1 | 9/2014 | Ortega et al. |
| 2015/0190553 A1 | 7/2015 | Constant et al. |
| 2015/0283306 A1 | 10/2015 | Constant et al. |
| 2015/0306227 A1 | 10/2015 | Cruise et al. |
| 2015/0306255 A1 | 10/2015 | Constant et al. |
| 2016/0166258 A1 | 6/2016 | Cruise et al. |

FOREIGN PATENT DOCUMENTS

| | | |
|---|---|---|
| EP | 809519 B1 | 12/1997 |
| EP | 1599258 B1 | 8/2008 |
| EP | 1601392 B1 | 4/2009 |
| WO | 1991/016057 A | 10/1991 |
| WO | 1994/003155 A1 | 2/1994 |
| WO | 1997/022365 A1 | 6/1997 |
| WO | 1997/026939 A1 | 7/1997 |
| WO | 1997/027888 A1 | 8/1997 |
| WO | 1998/001421 A1 | 1/1998 |
| WO | 1998/043615 A1 | 10/1998 |
| WO | 1999/023954 A1 | 5/1999 |
| WO | 1999/044538 A1 | 9/1999 |
| WO | 1999/056783 A1 | 11/1999 |
| WO | 1999/065401 A1 | 12/1999 |
| WO | 2000/027445 A1 | 5/2000 |
| WO | 2000/038651 A1 | 7/2000 |
| WO | 2000/074577 A1 | 12/2000 |
| WO | 2001/068720 A1 | 9/2001 |
| WO | 2002/005731 A1 | 1/2002 |
| WO | 2002/096302 A1 | 12/2002 |
| WO | 2003/043552 A1 | 5/2003 |
| WO | 2005/032337 A2 | 4/2005 |
| WO | 2007/016371 A2 | 2/2007 |
| WO | 2007/147145 A2 | 12/2007 |
| WO | 2009/086208 A2 | 7/2009 |
| WO | 2011/038291 A1 | 3/2011 |
| WO | 2011/053555 A1 | 5/2011 |
| WO | 2012/120138 A1 | 9/2012 |
| WO | 2012/145431 A3 | 10/2012 |
| WO | 2012/171478 A1 | 12/2012 |
| WO | 2013/158781 | 10/2013 |
| WO | 2015/153996 A1 | 10/2015 |
| WO | 2015/167751 A1 | 11/2015 |
| WO | 2015/167752 A1 | 11/2015 |

OTHER PUBLICATIONS

Chirila et al., Poly(2-hydroxyethyl metharcrylate) sponges ans implant materials: in vivo and in vitro evaluation of cellular invasion. Biomaterials, 14(1):26-38 (1993).

Constant et al., Preparation, Characterization, and Evaluation of Radiopaque Hydrogel Filaments for Endovascular Embolization. Journal of Biomedical Materials Research Part B: Applied Biomaterials, vol. 89B, No. 2, pp. 306-313 (2008).

Edleman et al., Controlled and modulated release of basic fibroblast growth factor. Biomaterials, vol. 12, pp. 619-626 (1991).

(56) References Cited

OTHER PUBLICATIONS

Elbert et al., Conjugate addition reactions combined with free-radical cross-linking for the design of materials for tissue engineering. Biomacromolecules, (2): 430-441 (2001).
European Search Opinion for EP Application No. 10819570 dated Mar. 31, 2014.
European Search Opinion for EP Application No. 10827370 dated Apr. 1, 2014.
Graves et al., Endovascular occlusion of the carotid or vertebral artery with temporary proximal flow arrest and mircoocoils: clinical results. AJNR Am. J. Neuroradiol., vol. 18, pp. 1201-1206 (1997).
Hoekstra, D., Hyaluronan-modified surfaces for medical devices. Medical Device & Diagnostic Industry, pp. 48-56.
Hogg et al., Interaction of platelet-derived growth factor with thrombospondin 1. Biochem. J. 326, pp. 709-716 (1997).
Horak et al., Hydrogels in endovascular embolization. II. Clinical use of spherical particles. Biomaterials, 7(6): 167-470 (1986).
Horak et al., New radiopaque polyHEMA-based hydrogel particles. J. Biomed. Matter Res., 34(2): 183-188 (1997).
Huang, et al., "Synthesis and Characterization of Self-Assembling Block Copolymers Containing Adhesive Molecules," Polymer Preprints, vol. 42, No. 2, 2001, pp. 147-148.
International Search Report dated Dec. 17, 2010 for International Patent Application No. PCT/US2010/053972.
International Search Report dated Feb. 5, 2009 for International Patent Application No. PCT/US2007/071395.
International Search Report dated Aug. 14, 2013 for International PCT Application No. PCT/US2013/037007 filed on Apr. 17, 2013.
International Search Report and Written Opinion dated Jun. 29, 2015 for International Application No. PCT/US2015/024289 filed on Apr. 3, 2015.
International Search Report and Written Opinion dated Jun. 29, 2015 for International Application No. PCT/US2015/024290 filed on Apr. 3, 2015.
International Search Report and Written Opinion dated Jul. 14, 2015 for International Application No. PCT/US2015/024284 filed on Apr. 3, 2015.
Kim, Drug release from pH-sensitive interpenetrating polymer networks hydrogel based on poly (ethylene glycol) Macromer and Poly (acrylic acid) prepared by UV Cured Method, ArchPharmRes, vol. 19(1), 1996, p. 18-22.
Klier, Self Associating Networks of Poly(methacrylic acid g-ethylene glycol) Marcomolecules 1990, vol. 23, 1990, p. 4944-4949.
Larsen et al., Hylan gel composition for percutaneous embolization. Journal of Biomedical Materials Research, vol. 25, Issue 6, pp. 699-710 (1991).
Latchaw et al., Polyvinyl foam embolization of vascular and neoplastic lesions of the head, neck, and spine. Radiology, 131: 669-679 (1979).
Li, Jian et al., Preparation of PEG/Aac copolymerric hydrogel and study of pH-sensitivity. Chemistry World, Issue 1, pp. 20-23 (2005).
Mellott, Michael B. et al., Release of protein from highly cross-linked hydrogels of poly(ethylene glycol) diacrylate fabricated by UV polymerization. Biomaterials, 22(2001) 929-941.
Murayama et al., Cellular responses of bioabsorbable polymeric material and guglielmi detachable coil in experimental aneurysms. Stroke, pp. 1120-1128 (2002).
Persidis, A., Tissue engineering. Nature Biotechnology, 17, pp. 508-510 (1999).
Schmutz et al., Embolization of cerebral arteriovenous malformations with silk: histopathologic changes and hemorrhagic complications. AJNR Am. J. Neuroradiol., vol. 18, pp. 1233-1237 (1997).
Schoenmakers, The effect of the linker on the hydrolysis rate of drug-linked ester bonds, J. Cont. Rel., 95, 2004, pp. 291-300.
Supplementary European Search Report for EP Application No. 10819570 dated Mar. 31, 2014.
Supplementary European Search Report for EP Application No. 10827370 dated Apr. 1, 2014.
Vinuela et al., Guglielmi detachable coil embolization of acute intracranial aneurysm: perioperative anatomical and clinical outcome in 403 patients. J. Neurosurg., vol. 86, pp. 475-482 (1997).
Woerly et al., Intracerebral implantation of hydrogel-coupled adhesion peptides: tissue reaction. Journal of Neural Transplantation & Plasticity, vol. 5, No. 4, pp. 245-255 (1995).
Written Opinion dated Aug. 14, 2013 for International PCT Application No. PCT/US2013/037007 filed on Apr. 17, 2013.
Zollikofer et al., A combination of stainless steel coil and compressed ivalon: a new technique for embolization of larger arteries and arteriovenous fistulas. Radiology, 138: 229-231 (1981).
Zollikofer et al., Therapeutic blockade of arteries using compressed invalon. Radiology, 136: 635-640 (1980).
Son et al., Preparation of properties of PEG-modified PHEMA hydrogel and the morphological effect. Macromolecular Research, vol. 14, No. 3, pp. 394-399 (2006).
International Search Report and Written Opinion dated Sep. 23, 2016 for International Application No. PCT/US2016/036924 filed on Jun. 10, 2016.
International PCT Application PCT/US2016/036924 dated Jun. 10, 2016.
U.S. Appl. No. 15/179,212 filed Jun. 10, 2016.
U.S. Appl. No. 15/252,089 filed Aug. 30, 2016.
U.S. Appl. No. 15/272,305 filed Sep. 21, 2016.

\* cited by examiner

EMBOLIZATION DEVICE CONSTRUCTED FROM EXPANSILE POLYMER

CROSS REFERENCE TO RELATED APPLICATIONS

This application is a continuation of U.S. patent application Ser. No. 13/553,275 filed on Jul. 19, 2012 entitled Embolization Device Constructed from Expansile Polymer, which is a continuation of U.S. patent application Ser. No. 11/764,111 filed Jun. 15, 2007 entitled Embolization Device Constructed From Expansile Polymer, now U.S. Pat. No. 8,377,091, which claims the benefit of U.S. Provisional Patent Application No. 60/814,309 filed on Jun. 15, 2006 entitled HESII: Embolization Device Constructed From Expansile Polymer, all of which are hereby incorporated herein in their entireties.

FIELD OF THE INVENTION

The present invention relates to devices for the occlusion of body cavities, such as the embolization of vascular aneurysms and the like, and methods for making and using such devices.

BACKGROUND OF THE INVENTION

The occlusion of body cavities, blood vessels, and other lumina by embolization is desired in a number of clinical situations. For example, the occlusion of fallopian tubes for the purposes of sterilization, and the occlusive repair of cardiac defects, such as a patent foramen ovale, patent ductus arteriosis, and left atrial appendage, and atrial septal defects. The function of an occlusion device in such situations is to substantially block or inhibit the flow of bodily fluids into or through the cavity, lumen, vessel, space, or defect for the therapeutic benefit of the patient.

The embolization of blood vessels is also desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been shown in the prior art. One approach that has shown promise is the use of thrombogenic microcoils. These microcoils may be made of biocompatible metal alloy(s) (typically a radio-opaque material such as platinum or tungsten) or a suitable polymer. Examples of microcoils are disclosed in the following patents: U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al; all of which are hereby incorporated by reference.

A specific type of microcoil that has achieved a measure of success is the Guglielmi Detachable Coil ("GDC"), described in U.S. Pat. No. 5,122,136—Guglielmi et al. The GDC employs a platinum wire coil fixed to a stainless steel delivery wire by a solder connection. After the coil is placed inside an aneurysm, an electrical current is applied to the delivery wire, which electrolytically disintegrates the solder junction, thereby detaching the coil from the delivery wire. The application of current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

A more recent development in the field of microcoil vaso-occlusive devices is exemplified in U.S. Pat. No. 6,299,619 to Greene, Jr. et al., U.S. Pat. No. 6,602,261 to Greene, Jr. et al., and co-pending U.S. patent application Ser. No. 10/631,981 to Martinez; all assigned to the assignee of the subject invention and incorporated herein by reference. These patents disclose vaso-occlusive devices comprising a microcoil with one or more expansile elements disposed on the outer surface of the coil. The expansile elements may be formed of any of a number of expansile polymeric hydrogels, or alternatively, environmentally-sensitive polymers that expand in response to a change in an environmental parameter (e.g., temperature or pH) when exposed to a physiological environment, such as the blood stream.

This invention is a novel vaso-occlusive device, a novel expansile element, and a combination thereof.

SUMMARY OF THE INVENTION

The present invention is directed to novel vaso-occlusive devices comprising a carrier member, novel expansile elements, and a combination thereof. Generally, the expansile element comprises an expansile polymer. The carrier member may be used to assist the delivery of the expansile element by providing a structure that, in some embodiments, allows coupling to a delivery mechanism and, in some embodiments, enhances the radiopacity of the device.

In one embodiment, the expansile polymer is an environmentally sensitive polymeric hydrogel, such as that described in U.S. Pat. No. 6,878,384, issued Apr. 12, 2005 to Cruise et al., hereby incorporated by reference. In another embodiment, the expansile polymer is a novel hydrogel comprised of sodium acrylate and a poly(ethylene glycol) derivative. In another embodiment, the expansile polymer is a hydrogel comprising a Pluronics® derivative.

In one embodiment, the expansile polymer is a novel hydrogel that has ionizable functional groups and is made from macromers. The hydrogel may be environmentally-responsive and have an unexpanded bending resistance of from about 0.1 milligrams to about 85 milligrams. The macromers may be non-ionic and/or ethylenically unsaturated.

In another embodiment, the macromers may have a molecular weight of about 400 to about 35,000, more preferably about 5,000 to about 15,000, even more preferably about 8,500 to about 12,000. In another embodiment, the hydrogel may be made of polyethers, polyurethanes, derivatives thereof, or combinations thereof. In another embodiment, the ionizable functional groups may comprise basic groups (e.g., amines, derivatives thereof, or combinations thereof) or acidic groups (e.g., carboxylic acids, derivatives thereof, or combinations thereof). If the ionizable functional groups comprise basic groups, the basic groups may be deprotonated at pHs greater than the pKa or protonated at pHs less than the pKa of the basic groups. If the ionizable functional groups comprise acidic groups, the acidic groups may be protonated at pHs less than the pKa or de-protonated at pHs greater than the pKa of the acidic groups.

In another embodiment, the macromers may comprise vinyl, acrylate, acrylamide, or methacrylate derivatives of poly(ethylene glycol), or combinations thereof. In another embodiment, the macromer may comprise poly(ethylene glycol) di-acrylamide. In another embodiment, the hydrogel is substantially free, more preferably free of unbound acrylamide.

In another embodiment, the macromers may be cross-linked with a compound that contains at least two ethylenically unsaturated moities. Examples of ethylenically unsaturated compounds include N, N'-methylenebisacrylamide, derivatives thereof, or combinations thereof. In another embodiment, the hydrogel may be prepared using a polymerization initiator. Examples of suitable polymerization initiators comprise N,N,N',N'-tetramethylethylenediamine, ammonium persulfate, azobisisobutyronitrile, benzoyl peroxides, derivatives thereof, or combinations thereof. The polymerization initiator may be soluble in aqueous or organic solvents. For example, azobisisobutyronitrile is not water soluble; however, water soluble derivatives of azobisisobutyronitrile, such as 2,2'-azobis(2-methylproprionamidine) dihydrochloride, are available. In another embodiment, the hydrogel may be substantially non-resorbable, non-degradable or both, at physiological conditions.

In another embodiment, the invention comprises a method for preparing an environmentally-responsive hydrogel for implantation in an animal. The method includes combining at least one, preferably non-ionic, macromer with at least one ethylenically unsaturated moiety, at least one macromer or monomer having at least one ionizable functional group and at least one ethylenically unsaturated moiety, at least one polymerization initiator, and at least one solvent to form a hydrogel. The solvent may include aqueous or organic solvents, or combinations thereof. In another embodiment, the solvent is water. Next, the hydrogel may be treated to prepare an environmentally-responsive hydrogel, preferably one that is responsive at physiological conditions. The ionizable functional group(s) may be an acidic group (e.g., a carboxylic acid, a derivative thereof, or combinations thereof) or a basic group (e.g., an amine, derivatives thereof, or combinations thereof). If the ionizable functional group comprises an acidic group, the treating step may comprise incubating the hydrogel in an acidic environment to protonate the acidic groups. If the ionizable functional group comprises a basic group, the treating step may comprise incubating the hydrogel in a basic environment to de-protonate the basic groups. In certain embodiments, it is preferable that the acidic groups are capable of being de-protonated or, conversely, the basic groups are capable of being protonated, after implantation in an animal.

In another embodiment, the ethylenically unsaturated macromer may have a vinyl, acrylate, methacrylate, or acrylamide group; including derivatives thereof or combinations thereof. In another embodiment, the ethylenically unsaturated macromer is based upon poly(ethylene glycol), derivatives thereof, or combinations thereof. In another embodiment, the ethylenically unsaturated macromer is poly(ethylene glycol) di-acrylamide, poly(ethylene glycol) di-acrylate, poly(ethylene glycol) di-methacrylate, derivatives thereof, or combinations thereof. In another embodiment, the ethylenically unsaturated macromer is poly(ethylene glycol) di-acrylamide. The ethylenically unsaturated macromer may be used at a concentration of about 5% to about 40% by weight, more preferably about 20% to about 30% by weight. The solvent may be used at a concentration of about 20% to about 80% by weight.

In another embodiment, the combining step also includes adding at least one cross-linking agent comprising an ethylenically unsaturated compound. In certain embodiments of the present invention, a cross-linker may not be necessary. In other words, the hydrogel may be prepared using a macromer with a plurality of ethylenically unsaturated moieties. In another embodiment, the polymerization initiator may be a reduction-oxidation polymerization initiator. In another embodiment, the polymerization initiator may be N,N,N',N'-tetramethylethylenediamine, ammonium persulfate, azobisisobutyronitrile, benzoyl peroxides, 2,2'-azobis(2-methylproprionamidine) dihydrochloride, derivatives thereof, or combinations thereof. In another embodiment, the combining step further includes adding a porosigen.

In another embodiment, the ethylenically unsaturated macromer includes poly(ethylene glycol) di-acrylamide, the macromer or monomer or polymer with at least one ionizable group and at least one ethylenically unsaturated group includes sodium acrylate, the polymerization initiator includes ammonium persulfate and N,N,N,',N' tetramethylethylenediamine, and the solvent includes water.

In another embodiment, the ethylenically unsaturated macromer has a molecular weight of about 400 to about 35,000 grams/mole, more preferably about 2,000 to about 25,000 grams/mole, even more preferably about 5,000 to about 15,000 grams/mole, even more preferably about 8,000 to about 12,500 grams/mole, and even more preferably about 8,500 to about 12,000 grams/mole. In another embodiment, the environmentally-responsive hydrogel is substantially non-resorbable, or non-degradable or both at physiological conditions. In certain embodiments, the environmentally-responsive hydrogel may be substantially free or completely free of unbound acrylamide.

In one embodiment, the carrier member comprises a coil or microcoil made from metal, plastic, or similar materials. In another embodiment, the carrier member comprises a braid or knit made from metal, plastic, or similar materials. In another embodiment, the carrier member comprises a plastic or metal tube with multiple cuts or grooves cut into the tube.

In one embodiment, the expansile element is arranged generally co-axially within the carrier member. In another embodiment, a stretch resistant member is arranged parallel to the expansile element. In another embodiment, the stretch resistant member is wrapped, tied, or twisted around the expansile element. In another embodiment, the stretch resistant member is positioned within the expansile element.

In one embodiment, the device comprising the expansile element and carrier member are detachably coupled to a delivery system. In another embodiment, the device is configured for delivery by pushing or injecting through a conduit into a body.

In one embodiment, the expansile element is environmentally sensitive and exhibits delayed expansion when exposed to bodily fluids. In another embodiment, the expansile element expands quickly upon contact with a bodily fluid. In another embodiment, the expansile element comprises a porous or reticulated structure that may form a surface or scaffold for cellular growth.

In one embodiment, the expansile element expands to a dimension that is larger than the diameter of the carrier member in order to provide enhanced filling of the lesion. In another embodiment, the expansile element expands to a dimension equal to or smaller than the diameter of the carrier member to provide a scaffold for cellular growth, release of therapeutic agents such as pharmaceuticals, proteins, genes, biologic compounds such as fibrin, or the like.

DESCRIPTION OF THE INVENTION

Figure 1:
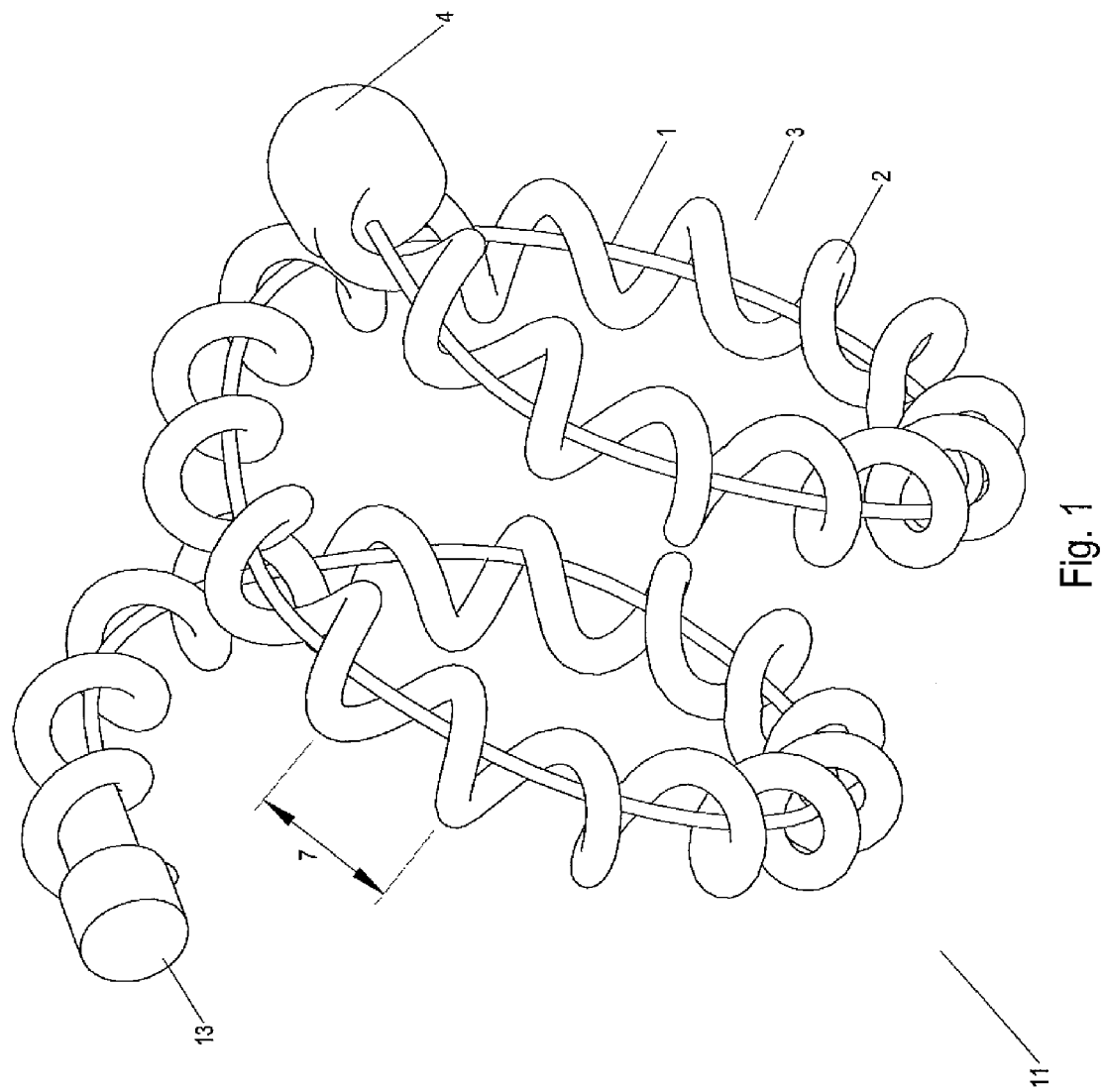
FIG. 1 is a perspective view showing one embodiment of the present invention prior to expansion of the expansile element.

As used herein, the term "macromer" refers to a large molecule containing at least one active polymerization site or binding site. Macromers have a larger molecular weight than monomers. For example, an acrylamide monomer has a molecular weight of about 71.08 grams/mole whereas a poly(ethylene glycol) di-acrylamide macromer may have a molecular weight of about 400 grams/mole or greater. Preferred macromers are non-ionic, i.e. they are uncharged at all pHs.

As used herein, the term "environmentally responsive" refers to a material (e.g., a hydrogel) that is sensitive to changes in environment including but not limited to pH, temperature, and pressure. Many of the expansile materials suitable for use in the present invention are environmentally responsive at physiological conditions.

As used herein, the term "non-resorbable" refers to a material (e.g., a hydrogel) that cannot be readily and/or substantially degraded and/or absorbed by bodily tissues.

As used herein, the term "unexpanded" refers to the state at which a hydrogel is substantially not hydrated and, therefore, not expanded.

As used herein, the term "ethylenically unsaturated" refers to a chemical entity (e.g., a macromer, monomer or polymer) containing at least one carbon-carbon double bond.

As used herein, the term "bending resistance" refers to the resistance exhibited by a sample (e.g., an unexpanded hydrogel) as it steadily and evenly is moved across a resistance-providing arm or vane. The maximum displacement of the resistance-providing arm or vane is measured at the point the sample bends and releases the resistance-providing arm or vane. That maximum displacement is converted to bending "resistance" or "stiffness" using conversions appropriate to the machine, its calibration, and the amount of resistance (e.g., weight), if any, associated with the resistance-providing arm or vane. Herein, the units of measure for bending resistance will be milligrams (mg) and essentially is the amount of force required to bend the sample.

Referring to FIG. 1-8, the invention is a device comprising an expansile element 1 and a carrier member 2. The expansile element 1 may be made from a variety of suitable biocompatible polymers. In one embodiment, the expansile element 1 is made of a bioabsorbable or biodegradable polymer, such as those described in U.S. Pat. Nos. 7,070,607 and 6,684,884, the disclosures of which are incorporated herein by reference. In another embodiment, the expansile element 1 is made of a soft conformal material, and more preferably of an expansile material such as a hydrogel.

In one embodiment, the material forming the expansile element 1 is an environmentally responsive hydrogel, such as that described in U.S. Pat. No. 6,878,384, the disclosure of which is incorporated herein by reference. Specifically, the hydrogels described in U.S. Pat. No. 6,878,384 are of a type that undergoes controlled volumetric expansion in response to changes in such environmental parameters as pH or temperature. These hydrogels are prepared by forming a liquid mixture that contains (a) at least one monomer and/or polymer, at least a portion of which is sensitive to changes in an environmental parameter; (b) a cross-linking agent; and (c) a polymerization initiator. If desired, a porosigen (e.g., NaCl, ice crystals, or sucrose) may be added to the mixture, and then removed from the resultant solid hydrogel to provide a hydrogel with sufficient porosity to permit cellular ingrowth. The controlled rate of expansion is provided through the incorporation of ethylenically unsaturated monomers with ionizable functional groups (e.g., amines, carboxylic acids). For example, if acrylic acid is incorporated into the crosslinked network, the hydrogel is incubated in a low pH solution to protonate the carboxylic acid groups. After the excess low pH solution is rinsed away and the hydrogel dried, the hydrogel can be introduced through a microcatheter filled with saline at physiological pH or with blood. The hydrogel cannot expand until the carboxylic acid groups deprotonate. Conversely, if an amine-containing monomer is incorporated into the crosslinked network, the hydrogel is incubated in a high pH solution to deprotonate amines. After the excess high pH solution is rinsed away and the hydrogel dried, the hydrogel can be introduced through a microcatheter filled with saline at physiological pH or with blood. The hydrogel cannot expand until the amine groups protonate.

In another embodiment, the material forming the expansile element 1 is may be an environmentally responsive hydrogel, similar to those described in U.S. Pat. No. 6,878,384; however, an ethylenically unsaturated, and preferably non-ionic, macromer replaces or augments at least one monomer or polymer. The Applicants surprisingly have discovered that hydrogels prepared in accordance with this embodiment can be softer and/or more flexible in their unexpanded state than those prepared in accordance with U.S. Pat. No. 6,878,384. Indeed, hydrogels prepared in accordance with this embodiment may have an unexpanded bending resistance of from about 0.1 mg to about 85 mg, about 0.1 mg to about 50 mg, about 0.1 mg to about 25 mg, about 0.5 mg to about 10 mg, or about 0.5 mg to about 5 mg. The Applicants also have discovered that ethylenically unsaturated and non-ionic macromers (e.g., poly(ethylene glycol) and derivatives thereof) may be used not only to prepare a softer unexpanded hydrogel; but, in combination with monomers or polymers containing ionizable groups, one that also may be treated to be made environmentally responsive. The surprising increase in unexpanded flexibility enables the hydrogels to be, for example, more easily deployed in an animal or deployed with reduced or no damage to bodily tissues, conduits, cavities, etceteras.

The hydrogels prepared from non-ionic macromers in combination with monomers or polymers with ionizable functional groups still are capable of undergoing controlled volumetric expansion in response to changes in environmental parameters. These hydrogels may be prepared by combining in the presence of a solvent: (a) at least one, preferably non-ionic, macromer with a plurality of ethylenically unsaturated moieties; (b) a macromer or polymer or monomer having at least one ionizable functional group and at least one ethylenically unsaturated moiety; and (c) a polymerization initiator. It is worthwhile to note that with this type of hydrogel, a cross-linking agent may not be necessary for cross-linking since, in certain embodiments, the components selected may be sufficient to form the hydrogel. As hereinbefore described, a porosigen may be added to the mixture and then removed from the resultant hydrogel to provide a hydrogel with sufficient porosity to permit cellular ingrowth.

The non-ionic macromer-containing hydrogels' controlled rate of expansion may be provided through the incorporation of at least one macromer or polymer or monomer having at least one ionizable functional group (e.g., amine, carboxylic acid). As discussed above, if the functional group is an acid, the hydrogel is incubated in a low pH solution to protonate the group. After the excess low pH solution is rinsed away and the hydrogel dried, the hydrogel can be introduced through a microcatheter, preferably filled with saline. The hydrogel cannot expand until the acid group(s) deprotonates. Conversely, if the functional group is an amine, the hydrogel is incubated in a high pH solution to deprotonate the group. After the excess high pH solution is rinsed away and the hydrogel dried, the hydrogel can be introduced through a microcatheter, preferably filled with saline. The hydrogel cannot expand until the amine(s) protonates.

More specifically, in one embodiment, the hydrogel is prepared by combining at least one non-ionic macromer having at least one unsaturated moiety, at least one macromer or monomer or polymer having at least one ionizable functional group and at least one ethylenically unsaturated moiety, at least one polymerization initiator, and a solvent. Optionally, an ethylenically unsaturated crosslinking agent and/or a porosigen also may be incorporated. Preferred concentrations of the non-ionic macromers in the solvent range from about 5% to about 40% (w/w), more preferably about 20% to about 30% (w/w). A preferred non-ionic macromer is poly(ethylene glycol), its derivatives, and combinations thereof. Derivatives include, but are not limited to, poly(ethylene glycol) di-acrylamide, poly(ethylene glycol) di-acrylate, and poly(ethylene glycol) dimethacrylate. Poly(ethylene glycol) di-acrylamide is a preferred derivative of poly(ethylene glycol) and has a molecular weight ranging from about 8,500 to about 12,000. The macromer may have less than 20 polymerization sites, more preferably less than 10 polymerization sites, more preferably about five or less polymerization sites, and more preferably from about two to about four polymerization sites. Poly(ethylene glycol) di-acrylamide has two polymerization sites.

Preferred macromers or polymers or monomers having at least one ionizable functional group include, but are not limited to compounds having carboxylic acid or amino moieties or, derivatives thereof, or combinations thereof. Sodium acrylate is a preferred ionizable functional group-containing compound and has a molecular weight of 94.04 g/mole. Preferred concentrations of the ionizable macromers or polymers or monomers in the solvent range from about 5% to about 40% (w/w), more preferably about 20% to about 30% (w/w). At least a portion, preferably about 10%-50%, and more preferably about 10%-30%, of the ionizable macromers or polymers or monomers selected should be pH sensitive. It is preferred that no free acrylamide is used in the macromer-containing hydrogels of the present invention.

When used, the crosslinking agent may be any multifunctional ethylenically unsaturated compound, preferably N,N'-methylenebisacrylamide. If biodegradation of the hydrogel material is desired, a biodegradable crosslinking agent may be selected. The concentrations of the crosslinking agent in the solvent should be less than about 1% w/w, and preferably less than about 0.1% (w/w).

As described above, if a solvent is added, it may be selected based on the solubilities of the macromer(s) or monomer(s) or polymer(s), crosslinking agent, and/or porosigen used. If a liquid macromer or monomer or polymer solution is used, a solvent may not be necessary. A preferred solvent is water, but a variety of aqueous and organic solvents may be used. Preferred concentrations of the solvent range from about 20% to about 80% (w/w), more preferably about 50% to about 80% (w/w).

Crosslink density may be manipulated through changes in the macromer or monomer or polymer concentration, macromer molecular weight, solvent concentration and, when used, crosslinking agent concentration. As described above, the hydrogel may be crosslinked via reduction-oxidation, radiation, and/or heat. A preferred type of polymerization initiator is one that acts via reduction-oxidation. Suitable polymerization initiators include, but are not limited to, N,N,N',N'-tetramethylethylenediamine, ammonium persulfate, azobisisobutyronitrile, benzoyl peroxides, 2,2'-azobis(2-methylpropionamidine) dihydrochloride, derivatives thereof, or combinations thereof. A combination of ammonium persulfate and N,N,N',N'-tetramethylethylenediamine is a preferred polymerization initiator for use in the macromer containing embodiments of the invention.

After polymerization is complete, the hydrogels of the present invention may be washed with water, alcohol or other suitable washing solution(s) to remove any porosigen(s), any unreacted, residual macromer(s), monomer(s), and polymer(s) and any unincorporated oligomers. Preferably this is accomplished by initially washing the hydrogel in distilled water.

The hydrogels of the present invention may be made environmentally-responsive by protonating or deprotonating the ionizable functional groups present on the hydrogel network, as discussed above. Once the hydrogel has been prepared and, if needed, washed, the hydrogel may be treated to make the hydrogel environmentally-responsive. For hydrogel networks where the ionizable functional groups are carboxylic acid groups, the hydrogel is incubated in a low pH solution. The free protons in the solution protonate the carboxylic acid groups on the hydrogel network. The duration and temperature of the incubation and the pH of the solution influence the amount of control on the expansion rate. In general, the duration and temperature of the incubation are directly proportional to the amount of expansion control, while the incubation solution pH is inversely proportional thereto.

It has been determined that incubation solution water content also affects expansion control. In this regard, higher water content enables greater hydrogel expansion and is thought to increase the number of protonation-accessible carboxylic acid groups. An optimization of water content and pH is required for maximum control on expansion rate. Expansion control, among other things, has an effect on device positioning/repositioning time. Typically, a positioning/repositioning time of about 0.1 to about 30 minutes is preferred for hydrogel devices in accordance with the present invention.

After incubation, the excess treating solution is washed away and the hydrogel material is dried. A hydrogel treated with the low pH solution has been observed to dry down to a smaller dimension than an untreated hydrogel. This effect is desirable since devices containing these hydrogels may be delivered through a microcatheter.

For hydrogel networks where the ionizable functional groups are amine groups, the hydrogel is incubated in a high pH solution. Unlike carboxylic acid functional groups, deprotonation occurs on the amine groups of the hydrogel network at high pH. Aside from incubation solution pH, the incubation is carried out similarly to that of the carboxylic acid containing hydrogels. In other words, the duration and temperature of the incubation and the pH of the solution are directly proportional to the amount of expansion control. After incubation is concluded, the excess treating solution is washed away and the hydrogel material is dried.

In a preferred embodiment, the expansile element 1 is an expansile hydrogel comprised of (a) at least one, preferably non-ionic, ethylenically unsaturated macromer or monomer or polymer having at least two crosslinkable groups; (b) at least one monomer and/or polymer which has at least one crosslinkable groups, and at least one moiety that is sensitive to changes in an environmental parameter; and (c) a polymerization initiator. In some embodiments, the monomers and polymers may be water soluble, while in other embodiments they may be non-water soluble. Suitable polymers for components (a) and (b) include poly(ethylene glycol), poly(ethlyene oxide), poly(vinyl alcohol), poly(propylene oxide), poly(propylene glycol), poly(ethylene oxide)-co-poly(propylene oxide), poly(vinyl pyrrolidinone), poly(amino acids), dextrans, poly(ethyloxazoline), polysaccharides, proteins, glycosaminoglycans, and carbohydrates, and derivatives thereof. The preferred polymer is poly(ethylene glycol) (PEG), especially for component (a). Alternatively, polymers that biodegrade partly or completely may be utilized.

One embodiment comprises combining in the presence of a solvent (a) about 5% to about 40% of a non-ionic, ethylenically unsaturated macromer or monomer or polymer; (b) about 5% to about 40% of an ethylenically unsaturated monomer or polymer with at least one ionizable functional group; and, (c) a polymerization initiator. Suitable ionizable, ethylenically unsaturated monomers include acrylic acid and methacrylic acid, as well as derivatives thereof. One suitable monomer having at least one ionizable functional group is sodium acrylate. Suitable macromers with two ethylenically unsaturated moities include poly(ethylene glycol) di-acrylate and poly(ethylene glycol) di-acrylamide, and poly(ethylene glycol) di-acrylamide, which have molecular weights ranging between 400 and 30,000 grams/mole. The use of macromers with a plurality of ethylenically unsaturated groups permits the elimination of the crosslinker, as the crosslinker functions are performed by the multi-functional polymer. In one embodiment, the hydrogel comprises, about 5% to about 40% sodium acrylate, about 5% to about 40% poly(ethylene glycol) di-acrylamide, and the remaining amount water.

A sodium acrylate/poly(ethylene glycol) di-acrylamide hydrogel is used to enhance the mechanical properties of the previously-described environmentally responsive hydrogel. Since a sodium acrylate/poly(ethylene glycol) di-acrylamide hydrogel is softer than a sodium acrylate/acrylamide hydrogel (e.g., the one utilized in Hydrogel Embolic System (HES) made by MicroVention, Aliso Viejo, Calif.), devices incorporating it may be more flexible. Due to the relative stiffness of the HES, MicroVention recommends pre-softening the device by soaking in warm fluid or steaming the implant. In addition, devices made from acrylamide are relatively straight before pre-softening because the stiffness of the acrylamide-based hydrogel prevents the carrier member (for the HES, a microcoil) from assuming its secondary configuration. Devices made from a sodium acrylate/poly(ethylene glycol) di-acrylamide hydrogel may not require pre-softening techniques such as soaking in warm fluid such as saline or blood or exposure to steam in order to form into a secondary configuration heat-set into the carrier member 2 or a similar carrier member. Thus, in embodiments comprising, for example, sodium acrylate and poly(ethylene glycol) di-acrylamide, a substantially continuous length of hydrogel disposed either within the lumen 3 of the carrier member 2 as shown in, for example, FIG. 1 or on a carrier element such as those shown in the Martinez '981 application or Greene '261, will form into the secondary configuration pre-formed into the carrier member without pre-treatment (e.g. exposure to steam, fluid, or blood). This makes the device easier to use because it allows elimination of the pre-treatment step and the device may be safer when deployed into the patient because a softer device is less likely to cause damage to the lesion.

EXAMPLE 3 g of acrylamide, 1.7 g of acrylic acid, 9 mg of bisacrylamide, 50 mg of N,N,N',N'-tetramethylethylenediamine, 15 mg of ammonium persulfate, and 15.9 g water were combined and polymerized in a 0.020 inch tube. The tubularized polymer was removed from the tubing to prepare Hydrogel 1 in accordance with U.S. Pat. No. 6,878,384.

4.6 g of poly(ethylene glycol) diacrylamide, 3.3 g of sodium acrylate, 100 mg of N,N,N',N'-tetramethylethylenediamine, 25 mg of ammonium persulfate, and 15.9 g water were combined and polymerized in a 0.020 inch tube. The tubularized polymer was removed from the tubing to prepare Hydrogel 2, in accordance with a macromer-containing hydrogel embodiment of the present invention.

A hydrogel identical to Hydrogel 2 was prepared; however, it additionally was acid treated in accordance with the present invention to prepare Hydrogel 2-Acid.

A large platinum microcoil has a 0.014 inch outer diameter and a 0.0025 inch filar. A small platinum microcoil has a 0.010 inch outer diameter and a 0.002 inch filar.

The bending resistance of the unexpanded hydrogel samples and the bending resistance of the microcoils were obtained using a Gurley 4171 ET tubular sample stiffness tester with a 5-gram counterweight attached to its measuring vane. The sample length was 1 inch. The average measured resistance and standard deviation of five replicates each are summarized in the following table.

| SAMPLE | MEASURED RESISTANCE, milligrams |
|---|---|
| Hydrogel 1 | 88 ± 13 |
| Hydrogel 2 | 23 ± 1 |
| Hydrogel 2-Acid | 1 ± 0 |

| SAMPLE | MEASURED RESISTANCE, milligrams |
|---|---|
| Large Platinum Coil | 5 ± 1 |
| Small Platinum Coil | 2 ± 1 |

The results show the large difference in relative stiffness between the first generation Hydrogel 1 (HES), the second generation macromer-containing Hydrogel 2, the second generation macromer-containing Hydrogel 2 that has been acid treated, and the microcoils. Hydrogel 1 is nearly 20 times stiffer than a large platinum microcoil whereas Hydrogel 2 is less than 5 times stiffer than a large platinum microcoil. The acid-treated Hydrogel 2 is less stiff than a large platinum microcoil and about as stiff as a small platinum microcoil. A skilled artisan will appreciate that much more flexible unexpanded macromer-containing hydrogels are provided by the methods and materials disclosed in the present invention. When used in a medical device, these hydrogels may result in a more flexible medical device as well.

In another embodiment, monomers are used to impart moieties to the expansile element 1 that are suitable for coupling bioactive compounds, for example anti-inflammatory agents such as corticosteroids (e.g. prednisone and dexamethasone); or vasodilators such as nitrous oxide or hydralazine; or anti-thrombotic agents such as aspirin and heparin; or other therapeutic compounds, proteins such as mussel adhesive proteins (MAPs), amino acids such as 3-(3,4-dihydroxyphenyl)-L-alanine (DOPA), genes, or cellular material; see U.S. Pat. No. 5,658,308, WO 99/65401, *Polymer Preprints* 2001, 42(2), 147 *Synthesis and Characterization of Self-Assembling Block Copolymers Containing Adhesive Moieties* by Kui Hwang et. al., and WO 00/27445; the disclosures of which are hereby incorporated by reference. Examples of moieties for incorporation into hydrogel materials include, but are not limited to, hydroxyl groups, amines, and carboxylic acids.

In another embodiment, the expansile element 1 may be rendered radiopaque by incorporation of monomers and/or polymers containing, for example, iodine, or the incorporation of radiopaque metals such as tantalum and platinum.

In some embodiments, the carrier member 2 is a flexible, elongate structure. Suitable configurations for the carrier member 2 include helical coils, braids, and slotted or spiral-cut tubes. The carrier member 2 may be made of any suitable biocompatible metal or polymer such as platinum, tungsten, PET, PEEK, Teflon, Nitinol, Nylon, steel, and the like. The carrier member may be formed into a secondary configuration such as helix, box, sphere, flat rings, J-shape, S-shape or other complex shape known in the art. Examples of appropriate shapes are disclosed in Horton U.S. Pat. No. 5,766,219; Schaefer application. Ser. No. 10/043,947; and Wallace U.S. Pat. No. 6,860,893; all hereby incorporated by reference.

As previously described, some embodiments of the instant invention may comprise polymers that are sufficiently soft and flexible that a substantially continuous length of the expansile element 1 will form into a secondary configuration similar to the configuration originally set into the carrier member 2 without pre-softening the device or exposing it to blood, fluid, or steam.

Figure 2:
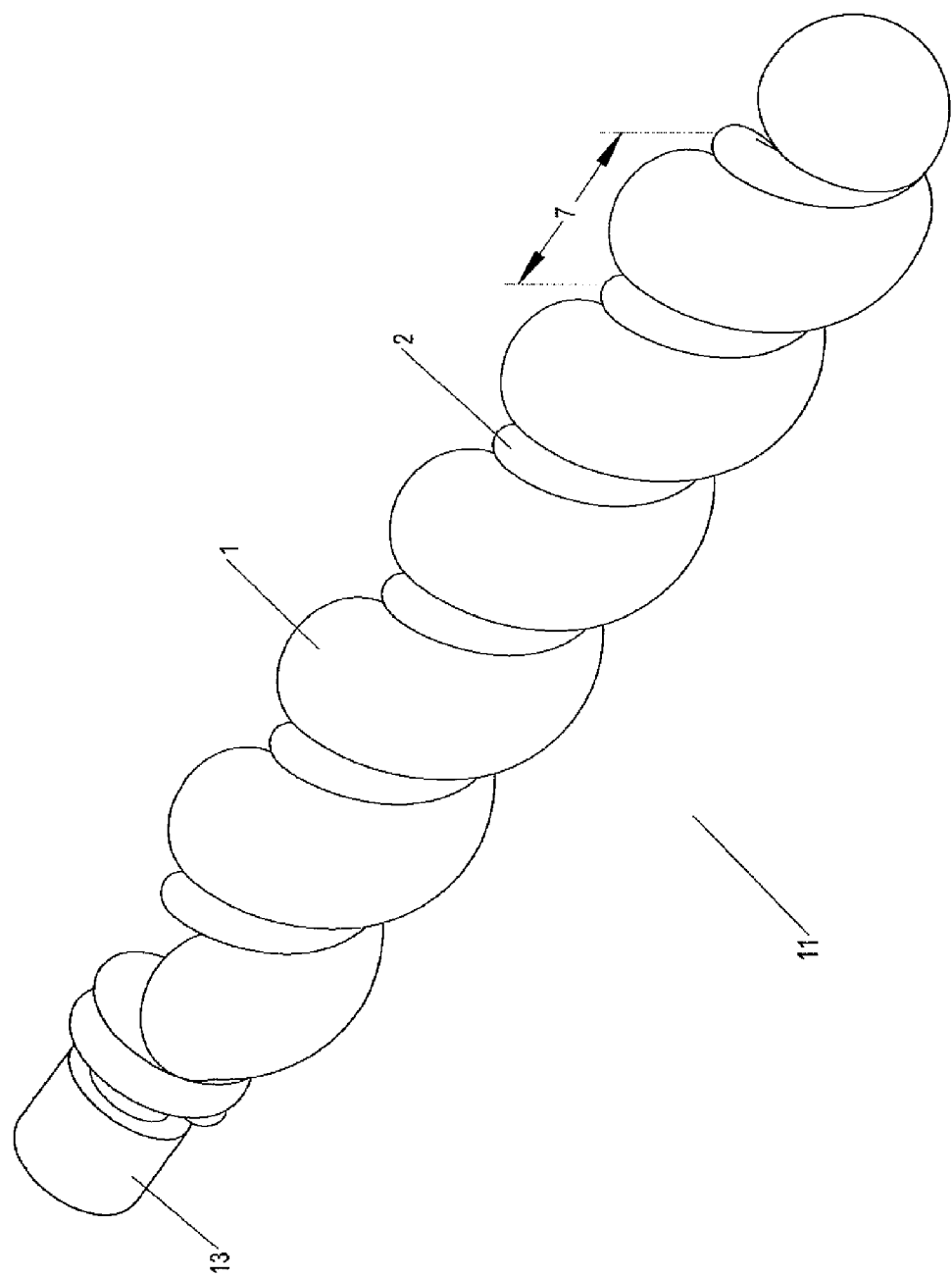
FIG. 2 is a perspective view showing a device similar to FIG. 1 in an expanded state.
Figure 8:
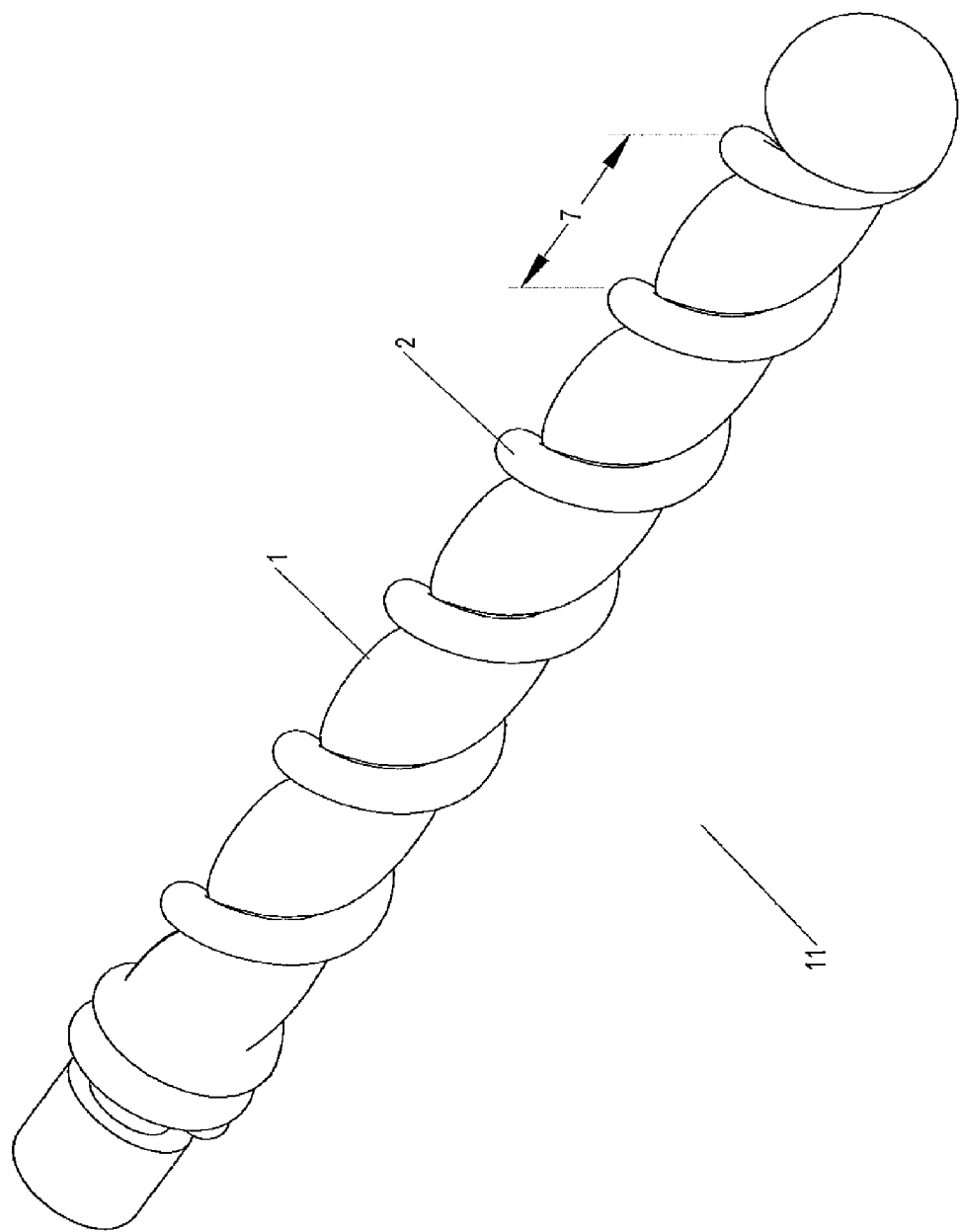
FIG. 8 is a perspective view of an alternative embodiment showing a device similar to those shown in FIG. 1 and FIG. 2 wherein the expansile element is not expanded to a diameter larger than the carrier member.

In some embodiments, the carrier member 2 incorporates at least one gap 7 that is dimensioned to allow the expansile element 1 to expand through the gap (one embodiment of this configuration is shown in FIGS. 1-2). In other embodiments, the carrier member 2 incorporates at least one gap 7 that allows the expansile element 1 to be exposed to bodily fluids, but the expansile element 1 does not necessarily expand through the gap (one embodiment of this configuration is shown in FIG. 8). In other embodiments, no substantial gap is incorporated into the carrier member 2. Rather, fluid is allowed to infiltrate through the ends of the device or is injected through a lumen within the delivery system and the expansile element 1 expands and forces its way through the carrier member 2.

In one embodiment shown in FIG. 1, the expansile element 1 comprises an acrylamide or poly(ethylene glycol)-based expansile hydrogel. The carrier member 2 comprises a coil. At least one gap 7 is formed in the carrier member 2. The expansile element 1 is disposed within the lumen 3 defined by the carrier member 2 in a generally coaxial configuration. A tip 4 is formed at the distal end of the device 11 by, for example, a laser, solder, adhesive, or melting the hydrogel material itself. The expansile element 1 may run continuously from the proximal end to the distal end, or it may run for a portion of the device then terminate before reaching the distal or proximal end, or both.

As an example, in one embodiment the device is dimensioned to treat a cerebral aneurysm. Those skilled in the art will appreciate that the dimensions used in this example could be re-scaled to treat larger or smaller lesions. In this embodiment, the expansile element 1 is about 0.001"–0.030" before expansion and about 0.002"–0.25" after expansion. The expansile element is, for example, approximately 5%-30% sodium acrylate, 10%-30% poly(ethylene glycol) di-acrylamide with a molecular weight ranging between 400 and 30,000 grams/mole, and the remainder water. Those skilled in the art will appreciate that the ratio of expansion could be controlled by changing the relative amounts of sodium acrylate, PEG di-acrylamide, and water. The carrier member 2 in this embodiment is a microcoil in the range of about 0.005"-0.035" in diameter. In an alternate embodiment, the microcoil diameter has a range of 0.008'-0.016'. The microcoil may have a filar in the range of 0.0005"-0.01". In an alternate embodiment, the filar range is 0.00075"-0.004". The implant 11 comprises at least one gap 7 ranging from 0.5 filars (0.00025") long to 20 filars (0.2") long. In an alternate embodiment, the gap range is between approximately 0.00025" to 0.005". In one preferred embodiment, the microcoil has a diameter of 0.012" and a 0.002" filar, with a gap 7 of 0.0013". A coupler 13 is placed near the proximal end to allow the implant 11 to be detachably coupled to a delivery system or pushed or injected through a catheter. Examples of delivery systems are found in co-pending application Ser. No. 11/212,830 to Fitz, U.S. Pat. No. 6,425,893 to Guglielmi, U.S. Pat. No. 4,994,069 to Ritchart, U.S. Pat. No. 6,063,100 to Diaz, and U.S. Pat. No. 5,690,666 to Berenstein; the disclosures of which are hereby incorporated by reference.

In this embodiment, the implant 11 is constructed by formulating and mixing the hydrogel material as previously described in order to form the expansile element 1. The carrier member 2 is wound around a helical or complex form, and then heat-set by techniques known in the art to form a secondary diameter ranging from 0.5 mm to 30 mm and a length ranging from 5 mm to 100 cm. After processing, washing, and optional acid treatment, the expansile element 1 is threaded through the lumen 3 of the carrier member 2. The distal end of the expansile element 1 is then tied, for example by forming a knot, to the distal end of the carrier member 2. Adhesive, such as UV curable adhesive or epoxy, may be used to further enhance the bond between the expansile element 1 and the carrier member 2 and to form the distal tip 4. Alternatively, the tip may be formed by, for example, a laser weld or solder ball.

Figure 7:
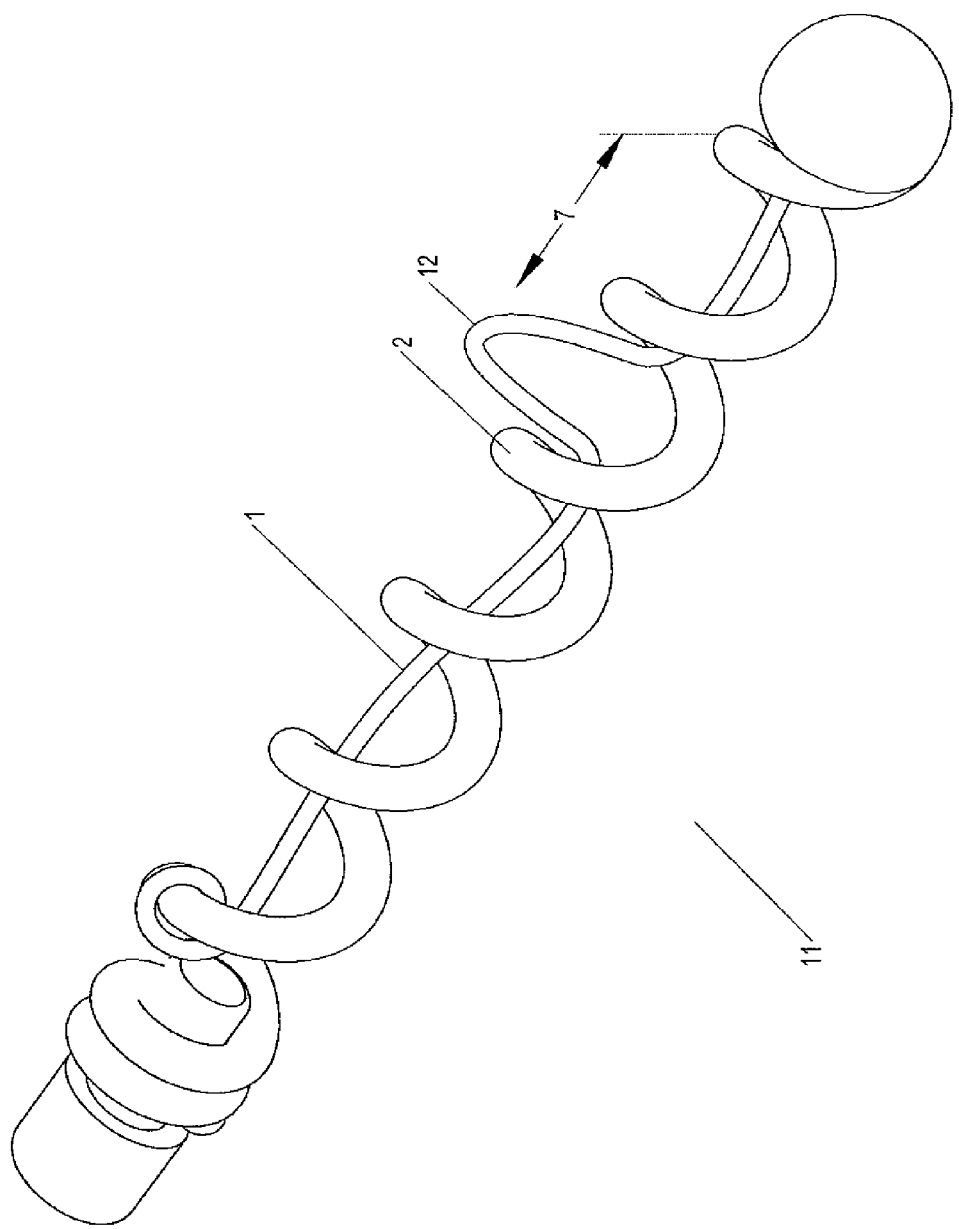
FIG. 7 is a perspective view of an alternative embodiment wherein the expansile element has formed a loop or fold outside the carrier member.

In some embodiments, depending on the size of the gap 7 and the ratio of expansion, loops or folds 12 may form as shown in FIG. 7 as the expansile element 1 expands. Although the loop or fold 12 may not affect the functionality of the device, in some embodiments it is desirable to prevent the loop or fold 12 from forming. This can be done by stretching the expansile element 1 either before placing it within the carrier member 2 or after the distal end of the expansile element 1 is secured to the carrier member 2. For example, once the distal end of the expansile element 1 is secured to the carrier member 2, the expansile element 1 is stretched to a final length between 101% to 1000% of its initial length (e.g. if the initial length is 1", the expansile element is stretched to 1.01"-10.0") or to a length sufficient to prevent loops from forming in the expansile element 1 after expansion. For example, in the previously described cerebral aneurysm treatment embodiment, the expansile element 1 is stretched to a final length, which is approximately 125%-600% of the initial length. In an alternate embodiment, the expansile element 1 is stretched to a final length, which is approximately 125%-300% of the initial length. In one preferred embodiment the expansile element is stretched to a final length that is approximately 267% of its initial length. After stretching, the expansile element 1 may be trimmed to match the length of the carrier member 2 and then bonded near the proximal end of the carrier member 2 by, for example, tying a knot, adhesive bonding, or other techniques known in the art.

Once the implant 11 has been constructed, it is attached to a delivery system previously described by methods known in the art. The device may also be exposed to, for example, e-beam or gamma radiation to cross-link the expansile element 1 and to control its expansion. This is described in U.S. Pat. No. 6,537,569 which is assigned to the assignee of this application and hereby incorporated by reference.

Previously, the secondary dimensions of prior devices (e.g. HES) are generally sized to a dimension 1-2 mm smaller than the dimension (i.e. volume) of the treatment site due to the relative stiffness of these devices. The increased flexibility and overall design of the implant 11 of the instant invention allows the secondary shape of the implant 11 to be sized to a dimension approximately the same size as the treatment site, or even somewhat larger. This sizing further minimizes the risk of the implant moving in or slipping out of the treatment site.

Prior implant devices, such as the HES device, currently provide the user with about 5 minutes of repositioning time. However, the implant 11 of the present invention increases the length of repositioning time. In some embodiments, the repositioning time during a procedure can be increased to about 30 minutes. In this respect, the user is provided with a longer repositioning time to better achieve a desired implant configuration FIG. 2 shows an implant 11 similar to that shown in FIG. 1 after the expansile element 1 has expanded through the gap 7 to a dimension larger than the carrier member 2.

Figure 3:
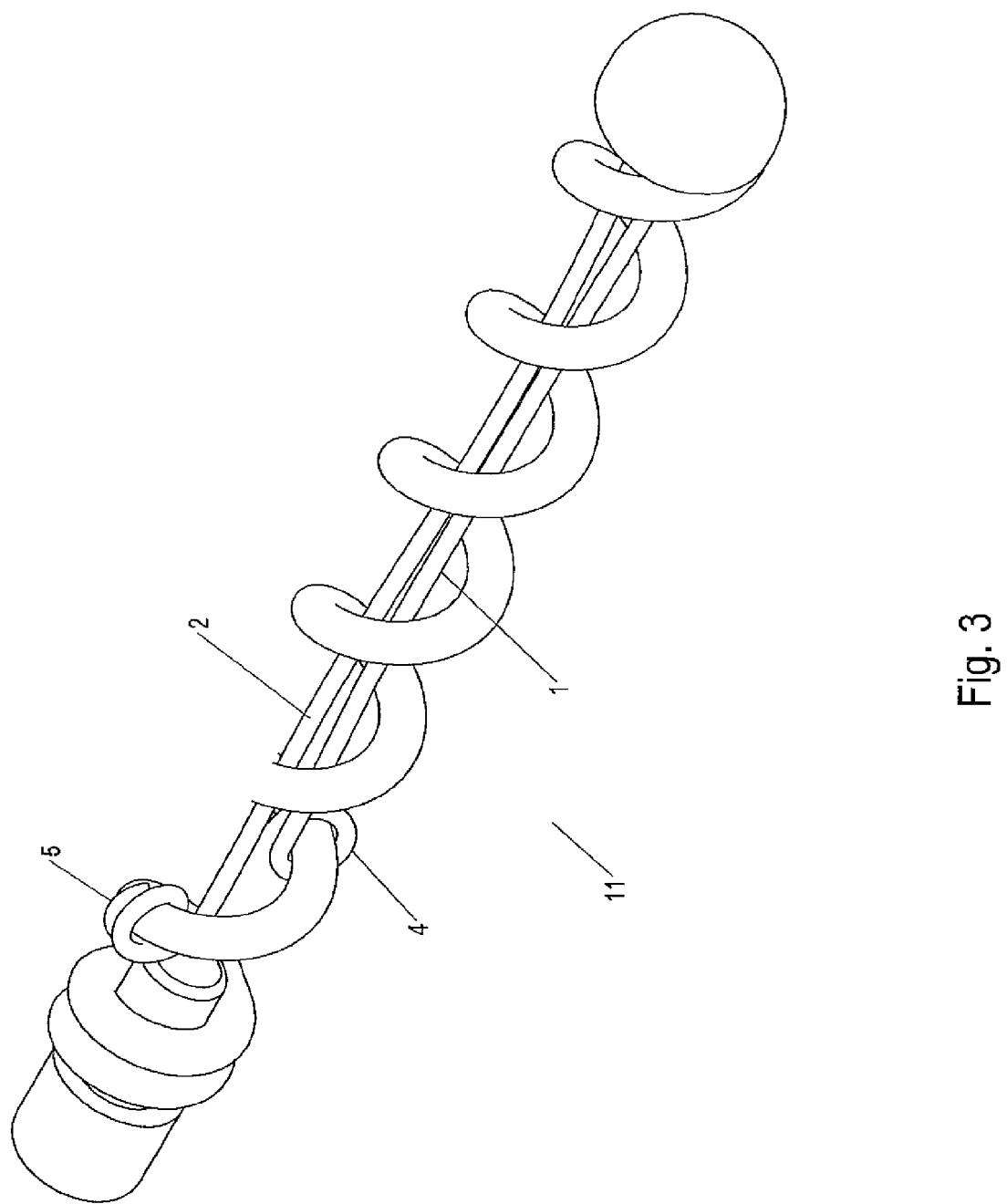
FIG. 3 is a perspective view of an alternative embodiment of the present invention.

FIG. 3 shows an implant 11 wherein multiple expansile elements 1 run somewhat parallel to each other through the carrier member 2. In one embodiment, this configuration is constructed by looping a single expansile element 1 around the tip 4 of the implant 11 and tying both ends of the expansile element 1 to the proximal end of the carrier member 2. In another embodiment, multiple strands of the expansile element 1 may be bonded along the length of the carrier member 2. The construction of these embodiments may also comprise stretching the expansile element 1 as previously described and/or forming gaps in the carrier member 2.

Figure 4:
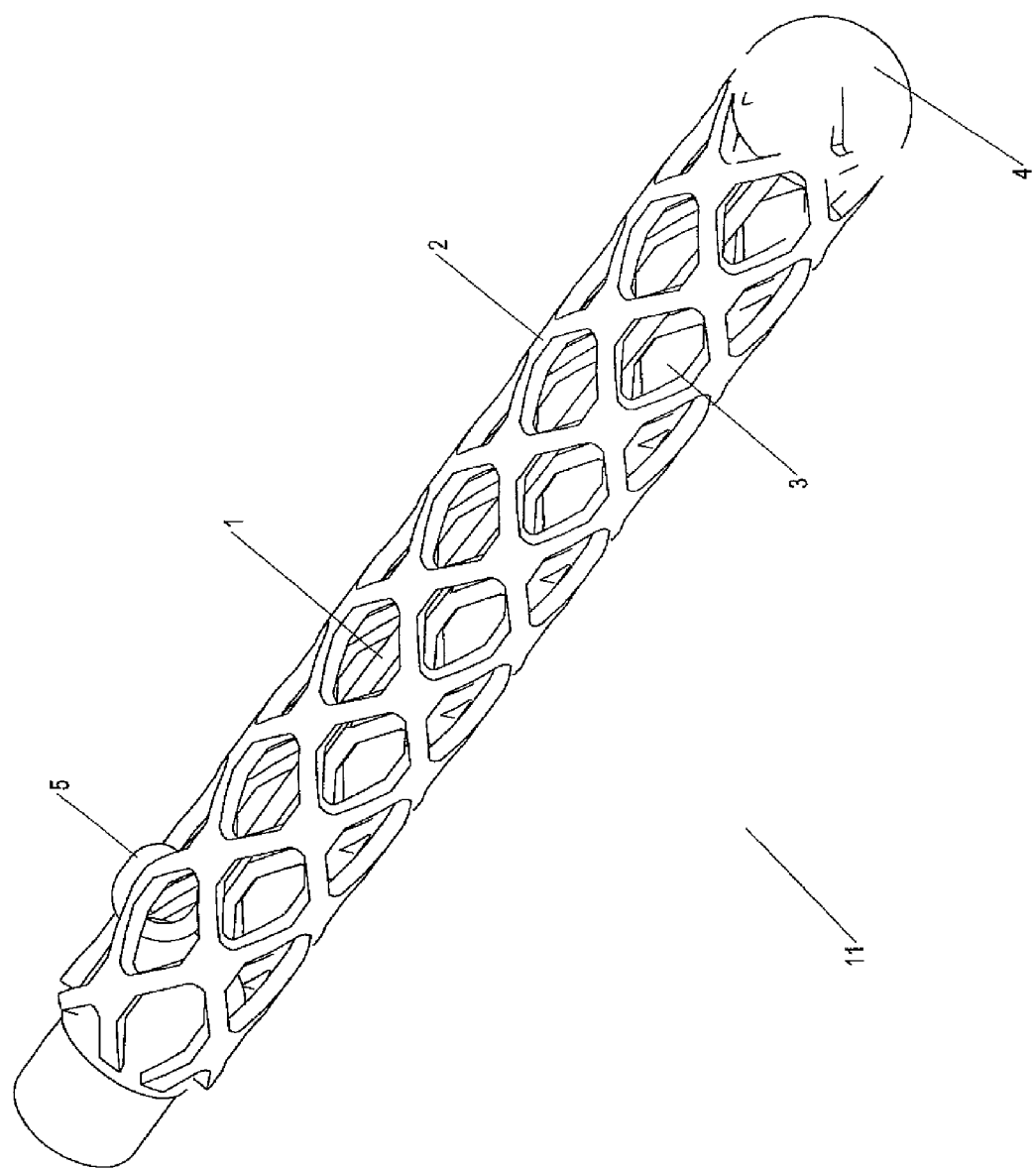
FIG. 4 is a perspective view of an alternative embodiment wherein the carrier member comprises a fenestrated tube, braid or knit.

FIG. 4 shows an embodiment wherein the implant 11 comprises a non-coil carrier member 2. In one embodiment, the carrier member 2 is formed by cutting a tube or sheet of plastic such as polyimide, nylon, polyester, polyglycolic acid, polylactic acid, PEEK, Teflon, carbon fiber or pyrolytic carbon, silicone, or other polymers known in the art with, for example; a cutting blade, laser, or water jet in order to form slots, holes, or other fenestrations through which the expansile element 1 may be in contact with bodily fluids. The plastic in this embodiment may also comprise a radiopaque agent such as tungsten powder, iodine, or barium sulfate. In another embodiment, the carrier member 2 is formed by cutting a tube or sheet of metal such as platinum, steel, tungsten, Nitinol, tantalum, titanium, chromium-cobalt alloy, or the like with, for example; acid etching, laser, water jet, or other techniques known in the art. In another embodiment, the carrier member 2 is formed by braiding, knitting, or wrapping metallic or plastic fibers in order to form fenestrations.

Figure 5:
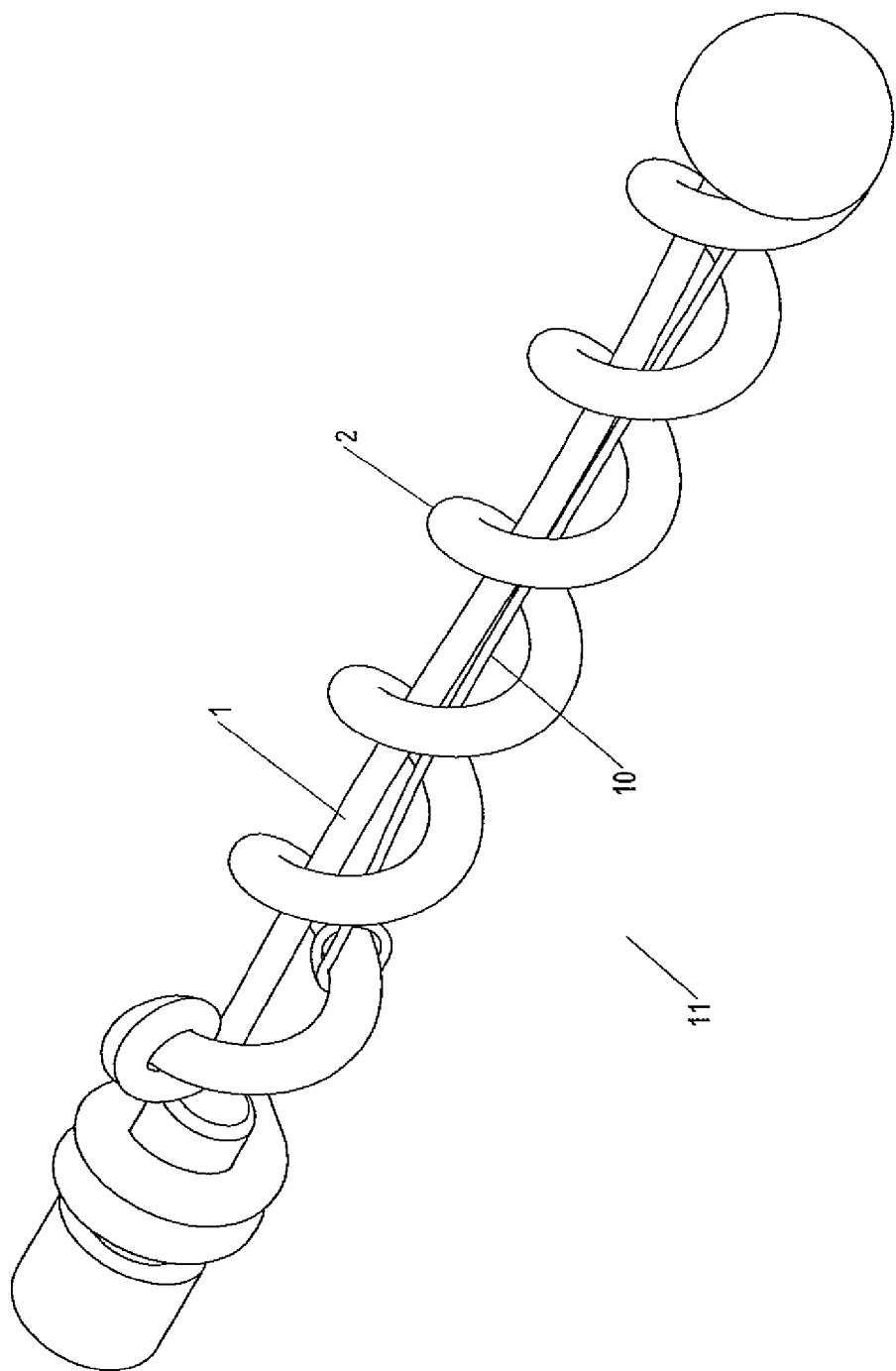
FIG. 5 is a perspective view of an alternative embodiment incorporating a stretch resistant member running approximately parallel to the expansile element.

FIG. 5 shows an implant 11 comprising a carrier member 2, an expansile element 1, and a stretch resistant member 10. The stretch resistant member 10 is used to prevent the carrier member 2 from stretching or unwinding during delivery and repositioning. The stretch resistant member 10 may be made from a variety of metallic or plastic fibers such as steel, Nitinol, PET, PEEK, Nylon, Teflon, polyethylene, polyolefin, polyolefin elastomer, polypropylene, polylactic acid, polyglycolic acid, and various other suture materials known in the art. Construction of the implant 11 may be by attaching the ends of the stretch resistant member 10 to the ends of the carrier member 2 as described by U.S. Pat. No. 6,013,084 to Ken and U.S. Pat. No. 5,217,484 to Marks both hereby incorporated by reference. Alternatively, the distal end of the stretch resistant member 10 may be attached near the distal end of the carrier member 2 and the proximal end to the stretch resistant member 10 attached to the delivery system as described in co-pending application. Ser. No. 11/212,830 to Fitz.

Figure 6:
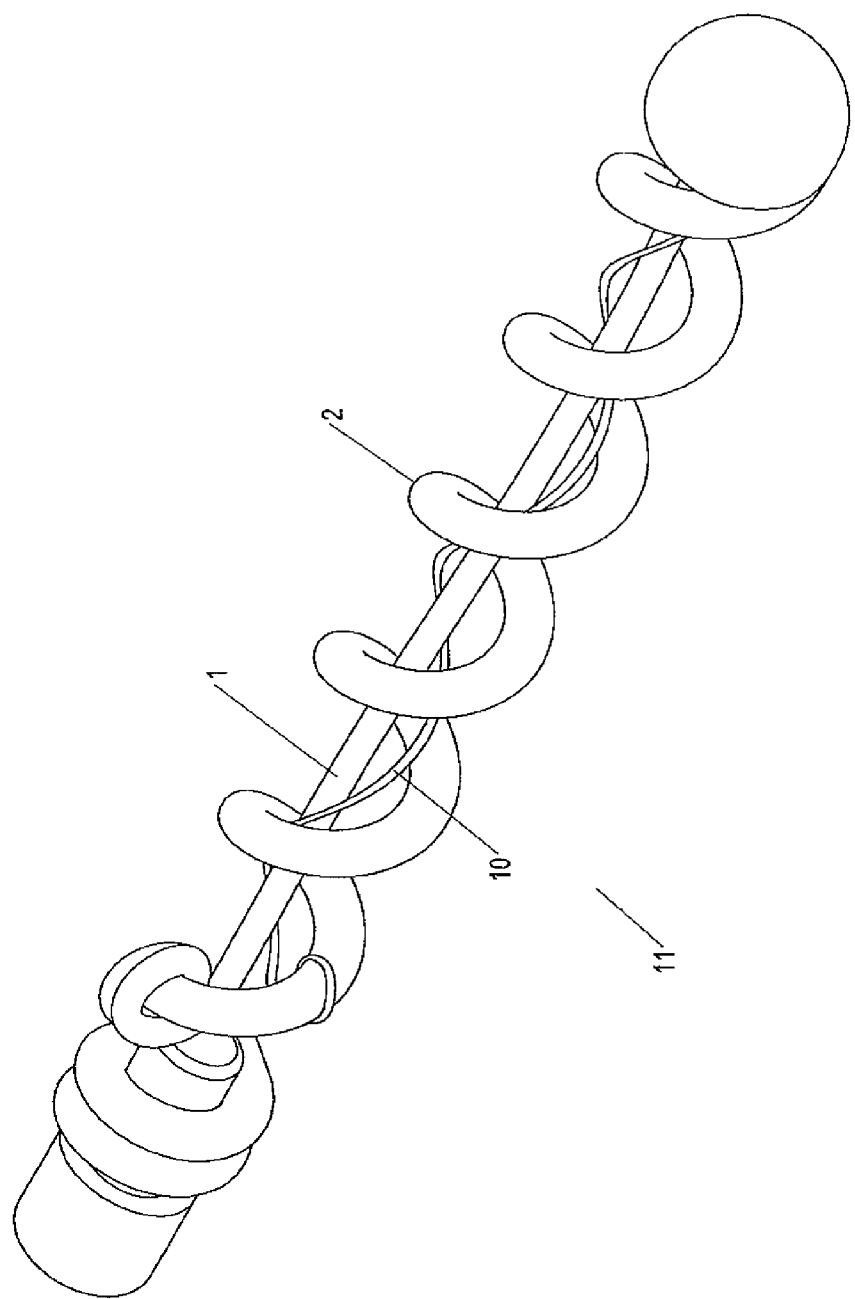
FIG. 6 is a perspective view of an alternative embodiment incorporating a stretch resistant member approximately intertwined with the expansile element.

FIG. 6 is an alternative embodiment comprising a stretch resistant member 10 wrapped around, tied to, or intertwined with the expansile element 1. This may occur over the length of the expansile element 1, or the wrapping or tying may be in only one area to facilitate bonding the expansile element 1 to the carrier element 2 by using the stretch resistant member 10 as a bonding element.

FIG. 7 shows a loop or fold 12 of the expansile element 1 protruding outside the carrier element 2. In some embodiments, it may be desirable to avoid this condition by, for example, stretching the expansile element 1 as previously described. This would be done, for example, in embodiments configured for delivery through a small microcatheter to prevent the implant 11 from becoming stuck in the microcatheter during delivery. In other embodiments, slack may be added to the expansile element 1 so that the loop or fold will be pre-formed into the implant 11. This would be done in embodiments where, for example, a large amount of volumetric filling were necessary because the loops or folds would tend to increase the total length of the expansile element 1.

FIG. 8 shows an embodiment wherein the expansile element 1 is configured to expand to a dimension larger than its initial dimension, but smaller than the outer dimension of the carrier member 2. This may be done by adjusting the ratio of, for example, PEG di-acrylamide to sodium acrylate in embodiments wherein the expansile element 1 comprises a hydrogel. Alternatively, a relatively high dose of radiation could be used to cross-link the expansile element 1, thus limiting its expansion. Embodiments such as shown in FIG. 8 are desirable when low volumetric filling is necessary and it is desirable to have a substrate for tissue growth and proliferation that the expansile element 1 provides. In an embodiment used to treat cerebral aneurysms, this configuration would be used as a final or "finishing" coil, or in devices dimensioned to treat small (under 10 mm diameter) aneurysms, or as a first "framing" or 3-D coil placed. In one embodiment, the expansile element 1 comprises a hydrogel incorporating a porosigen as previously described to provide a reticulated matrix to encourage cell growth and healing. Incorporating, for example, growth hormones or proteins in the expansile element 1 as previously described may further enhance the ability of the implant 11 to elicit a biological response.

In one embodiment of the invention a vaso-occlusive device comprises an expansile polymer element having an outer surface, a carrier member that covers at least a portion of the outer surface of the expansile polymer element, and wherein no carrier is disposed within the outer surface of the expansile element.

In another embodiment, a vaso-occlusive device comprises a coil having a lumen and a hydrogel polymer having an outer surface wherein the hydrogel polymer is disposed within the lumen of the coil and wherein the hydrogel polymer does not contain a coil within the outer surface of the hydrogel polymer.

In another embodiment, a vaso-occlusive device comprises a carrier member formed into a secondary configuration and an expansile element, wherein the expansile element is made from a polymer formulated to have sufficient softness that the expansile element will substantially take the shape of the secondary configuration formed into the carrier member without pre-treatment.

In another embodiment, a vaso-occlusive device comprises a carrier member formed into a secondary configuration and a substantially continuous length of hydrogel, wherein the device will substantially take the shape of the secondary configuration formed into the carrier member without pre-treatment.

In another embodiment, a vaso-occlusive device comprises a microcoil having an inner lumen and an expansile element disposed within the inner lumen. In this embodiment the expansile element comprises a hydrogel selected from the group consisting of acrylamide, poly(ethylene glycol), Pluronic, and poly(propylene oxide).

In another embodiment, a vaso-occlusive device comprises a coil and a hydrogel polymer disposed at least partially within the coil wherein the hydrogel has an initial length and wherein the hydrogel polymer has been stretched to a second length that is longer than the initial length.

In another embodiment, a vaso-occlusive device comprises an expansile element and a carrier member defining an inner lumen, wherein the expansile element is disposed within the inner lumen of the carrier member and wherein the expansile element has been stretched to a length sufficient to prevent a loop of the expansile element from protruding through the carrier member.

The invention disclosed herein also includes a method of manufacturing a medical device. The method comprises providing a carrier member having an inner lumen and an expansile element, inserting the expansile element into the inner lumen of the carrier member, and stretching the expansile element.

In another embodiment, a vaso-occlusive device comprises an expansile element encapsulated by a carrier element, wherein said expansile element is comprised substantially entirely and substantially uniformly of material having an expansile property.

In another embodiment, a vaso-occlusive device comprises a carrier element and an expansile element wherein the carrier element has a secondary shape that is different from its primary shape and wherein the expansile element is sufficiently flexible in a normal untreated state to conform with the secondary shape of the carrier.

In another embodiment, a vaso-occlusive device includes a carrier and an expansile element wherein the expansile element is fixed to the carrier in a manner such that the expansile element is in a stretched state along the carrier.

In another embodiment, a vaso-occlusive device includes a carrier having a plurality of gaps along the carrier and an expansile element positioned along an inside envelope of the carrier and wherein the expansion of the expansile element is controlled such that the expansile element expands into the gaps but not beyond the external envelope of the carrier.

In another embodiment, a vaso-occlusive device includes a carrier member and an expansile element wherein the expansile element is comprised of multiple strands extending along the carrier.

In another embodiment, a vaso-occlusive device includes a carrier and an expansile member wherein the carrier is a non-coiled cylindrically shaped structure and wherein said expansile member is disposed inside said carrier.

In another embodiment, a vaso-occlusive device includes a carrier and an expansile member and a stretch resistant member; said expansile member and said stretch resistant member being disposed in an internal region of the carrier and wherein the stretch resistant member is in tension on said carrier.

The invention disclosed herein also includes a method of treating a lesion within a body. The method comprises providing a vaso-occlusive device comprising a carrier member and an expansile element wherein the carrier member is formed into a secondary configuration that is approximately the same diameter as the lesion and inserting the vaso-occlusive device into the lesion.

Although preferred embodiments of the invention have been described in this specification and the accompanying drawings, it will be appreciated that a number of variations and modifications may suggest themselves to those skilled in the pertinent arts. Thus, the scope of the present invention is not limited to the specific embodiments and examples described herein, but should be deemed to encompass alternative embodiments and equivalents.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An occlusion device consisting essentially of:
an elongated, solid expansile element, that is flexible in an untreated state, consisting essentially of a poly(ethylene glycol) macromer and a pH sensitive monomer; and
a carrier element comprising a plurality of loops forming a helical shape disposed around the expansile element
wherein the elongated, solid, flexible expansile element is secured to the carrier element in a stretched configuration that is between about 125% and about 600% of its initial length.

2. The occlusion device of claim 1, wherein the carrier element is between about 0.005 inches and about 0.035 inches in diameter.

3. The occlusion device of claim 1, wherein the pH sensitive monomer is sodium acrylate.

4. The occlusion device of claim 1, wherein the plurality of loops are spaced by gaps.

5. The occlusion device of claim 4, wherein at least one gap is configured to allow the elongated expansile element to expand through the at least one gap.

6. The occlusion device of claim 5, wherein the at least one gap has a distance of about 0.00025 inches to about 0.2 inches.

7. The occlusion device of claim 6, wherein the at least one gap has a distance of about 0.00025 inches to about 0.005 inches.

8. The occlusion device of claim 5, wherein the at least one gap has a distance of about 0.0013 inches.

9. A method of treating a lesion comprising:
providing an occlusion device consisting essentially of
a carrier member, and
an elongated, solid expansile element, that is flexible in an untreated state, consisting essentially of a poly(ethylene glycol) macromer and a pH sensitive monomer to the lesion
wherein the elongated, solid expansile element is secured to the carrier member in a stretched configuration that is between about 125% and about 600% of its initial length and the carrier member is formed into a secondary configuration that is approximately the same diameter as the lesion.

10. The method of claim 9, wherein the poly(ethlyene glycol) macromer has a molecular weight of about 400 grams/mole to about 35,000 grams/mole.

11. The method of claim 9, wherein the carrier element is between about 0.005 inches and about 0.035 inches in diameter.

12. The method of claim 9, wherein the pH sensitive monomer is sodium acrylate.

13. The method of claim 9, wherein the carrier element comprises a plurality of loops forming a helical shape disposed around the expansile element.

14. The method of claim 13, wherein the plurality of loops are spaced by gaps.

15. The method of claim 14, wherein at least one gap is configured to allow the elongated, solid, expansile element to expand through the at least one gap.

16. The method of claim 15, wherein the at least one gap has a distance of about 0.00025 inches to about 0.2 inches.

17. The method of claim 16, wherein the at least one gap has a distance of about 0.00025 inches to about 0.005 inches.

18. The method of claim 15, wherein the at least one gap has a distance of about 0.0013 inches.

* * * * *